United States Patent [19]

Hayashi et al.

[11] Patent Number: 4,914,378
[45] Date of Patent: Apr. 3, 1990

[54] METHOD AND APPARATUS FOR INSPECTING SURFACE DEFECTS

[75] Inventors: Makoto Hayashi; Masahiro Ootaka; Akisuke Naruse; Kazuo Takaku, all of Hitachi, Japan

[73] Assignee: Hitachi, Ltd., Tokyo, Japan

[21] Appl. No.: 235,683

[22] PCT Filed: Oct. 16, 1987

[86] PCT No.: PCT/JP87/00789
§ 371 Date: Jun. 20, 1988
§ 102(e) Date: Jun. 20, 1988

[87] PCT Pub. No.: WO88/02857
PCT Pub. Date: Apr. 21, 1988

[30] Foreign Application Priority Data

Nov. 21, 1986 [JP] Japan ............... 61-278163
Oct. 20, 1988 [JP] Japan ............... 61-247428

[51] Int. Cl.⁴ .............. G01R 27/14; G01R 27/26; G01N 27/82
[52] U.S. Cl. .............. 324/696; 324/263; 324/691
[58] Field of Search .............. 324/64, 65 R, 65 LR, 324/65 P, 263

[56] References Cited

U.S. PATENT DOCUMENTS

| 4,656,595 | 4/1987 | Hognestad | 324/64 |
| 4,683,419 | 7/1987 | Neuelman | 324/263 |
| 4,764,970 | 8/1988 | Hayashi et al. | 324/64 |
| 4,789,829 | 12/1988 | Stribling | 324/263 |

FOREIGN PATENT DOCUMENTS 0024804 2/1982 Japan ............... 324/263

OTHER PUBLICATIONS

IBM Technical Disclosure, H. Hova, Measuring Thickness and Resistance of Semiconductor Layers, vol. 6, No. 2, Jul. 1963.

Primary Examiner—Reinhard J. Eisenzopf
Assistant Examiner—Jose M. Solis
Attorney, Agent, or Firm—Antonelli, Terry & Wands

[57] ABSTRACT

A method and an apparatus for detecting defects in the surface of a metal material relying upon the potential drop method. Namely, a method of precisely determining the shape of crack from a distribution of potential differences in the vicinity of crack by arranging power supplying electrodes and measuring electrodes on the surface of the metal material in the form of a matrix, and switching the electrodes that supply electric current and the electrodes that measure potential differences to measure distributions of potential differences in many directions, and an apparatus for detecting surface defects relying upon the potential drop method. In the apparatus for detecting surface defects, the arrangement of power supplying electrodes and supply currents are optimized to precisely detect the shape of crack in the surface.

9 Claims, 24 Drawing Sheets

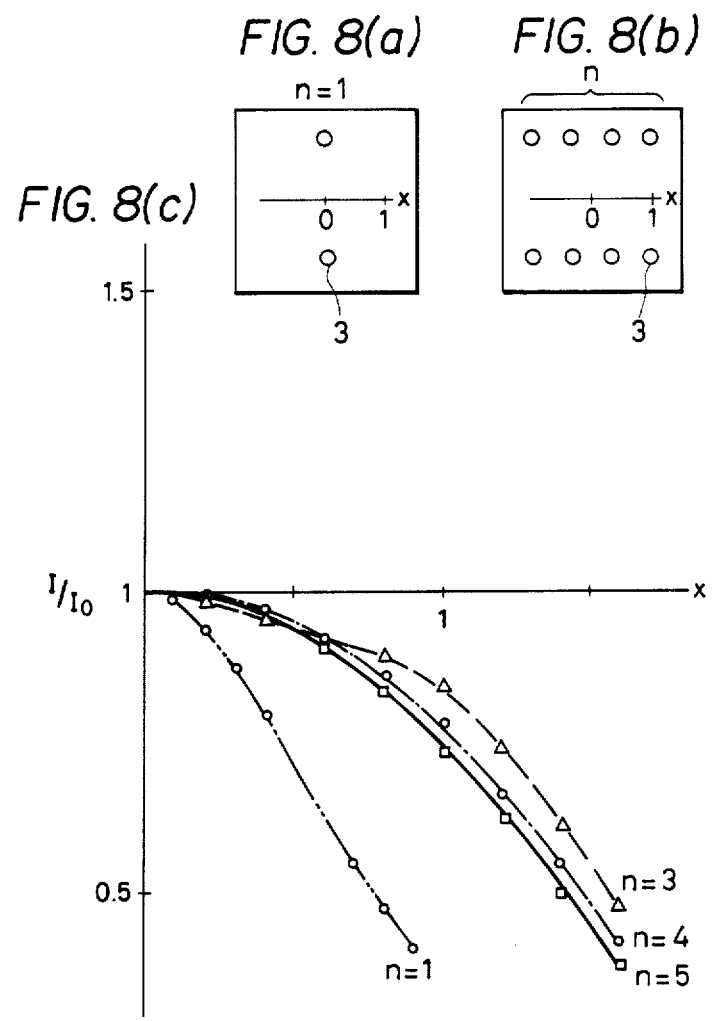

METHOD AND APPARATUS FOR INSPECTING SURFACE DEFECTS

TECHNICAL FIELD

The present invention relates to an apparatus for finding defects such as cracks that are initiated in metal materials and to a method thereof, and more specifically to an apparatus for precisely detecting the shape of crack and to a method thereof.

BACKGROUND ART

A potential method has heretofore been employed for detecting defects such as cracks were initiated in the metal materials. The potential drop method has been described, for example, in Japanese Patent Publication No. 2593/1975 and Japanese Patent Laid-Open No. 160054/1982.

The conventional apparatus for detecting defects on the surfaces of materials based upon the potential drop method employs a so-called four-terminal method. According to the four-terminal method which employs a probe in which are arranged in alignment a pair of power supplying electrodes and a pair of potential difference-measuring electrodes on the inside thereof, the surfaces of metallic structural members are scanned to measure the change in the potential distribution thereby to detect surface defects such as cracks. That is, the potential difference in a flawless region is used as a reference potential, and it is determined that a defect exists in a place if the potential difference there is greater than the reference potential.

In a large metal structure, initiation of surface cracks does not mean that its life has expired; i.e., the structure in many cases can be used for considerably extended periods of time even after defects have been initiated. The life after the surface defects have been initiated may often be longer than the period before the defects are initiated. It is therefore important to monitor the progress of surface defects from the standpoint of using the structure effectively for extended periods of time maintaining safety.

According to the conventional apparatus having a pair of power supplying electrodes, however, the electric current is not uniformly distributed due to a change in the shape of a member in a measuring region and makes it difficult to determine the reference potential for measurement. Furthermore, determination of the shapes of surface defects lacks precision which makes it difficult to precisely monitor the growth of surface defects. Due to the spread of current, furthermore, inspection is affected by the change of shapes near the measuring regions and by the neighboring defects.

DISCLOSURE OF INVENTION

The object of the present invention is to provide a novel method of and apparatus for detecting surface defects, which is capable of monitoring defects in the surface of a metal material maintaining high precision.

It is a further object of the invention to provide a novel method and apparatus for inspecting surface defects wherein power supplying electrodes are formed in a plural pairs maintaining a freedom of displacement, and a electrode position control unit is provided which causes said power supplying electrode pairs to undergo displacement to determine their positions based upon the current distribution on the inside of said pairs of power supply electrodes, and wherein a non-uniformity signal of current distribution due to a change of shape of the measuring region is received by said electrodes position control unit which produces control signals to change the positions of each of the pairs of power supplying electrodes to offset the non-uniformity, in order to uniformalize the current distribution.

Another object of the invention is to provide a novel method and apparatus for inspecting surface defects wherein power supplying electrodes are formed in a plurality of pairs, and a current control unit is provided to change currents that will be supplied to each of the pairs of power supplying electrodes depending upon the current distribution on the inside of said pairs of power supplying electrodes, and wherein a non-uniformity signal of current distribution is received by the current control unit which produces control signals to change currents that will be supplied to the pairs of power supply electrodes to offset the non-uniformity, in order to uniformalize the current distribution.

A yet further object of the invention is to provide a novel method and apparatus for inspecting surface defects wherein power supplying electrodes are formed in a plural pairs, potential difference-measuring electrode pairs are formed maintaining a freedom of displacement, and a measuring region control unit is provided to determine only those regions where the current distribution is nearly uniform on the inside of the pairs of power supplying electrodes to be the regions that are to be measured and scanned by the pairs of potential difference-measuring electrodes, in order to automatically detect defects only in the regions where the potential distribution is uniform.

Still another object is to provide a novel method of detecting the shape of defects by applying a direct current to the surface of a material to be inspected through a pair of power supplying electrodes that are spaced apart from each other, and by providing one or more pairs of potential difference-measuring electrodes between said pair of power supplying electrodes to measure potential difference in order to detect the shape of defect from said potential difference with an improvement wherein electrodes that serve both as power supplying electrodes and potential difference-measuring electrodes are arranged in the form of a matrix on the surface of a structure in which cracks may be initiated, and electrodes to be served with electric power and electrodes for measuring the potential difference are switched to measure the potential difference distribution, in order to measure the potential difference distribution in various directions on the surfaces of the material to be inspected thereby to precisely determine the shape of crack in the surface.

BRIEF DESCRIPTION OF DRAWINGS

FIGS. 8(a) and 8(b) show an arrangement of pairs of power supplying electrodes.

FIG. 8(c) is a diagram illustrating a relationship between the number n of the pairs of power supplying electrodes and the current distribution;

BEST MODE FOR CARRYING OUT THE INVENTION

Figure 1:
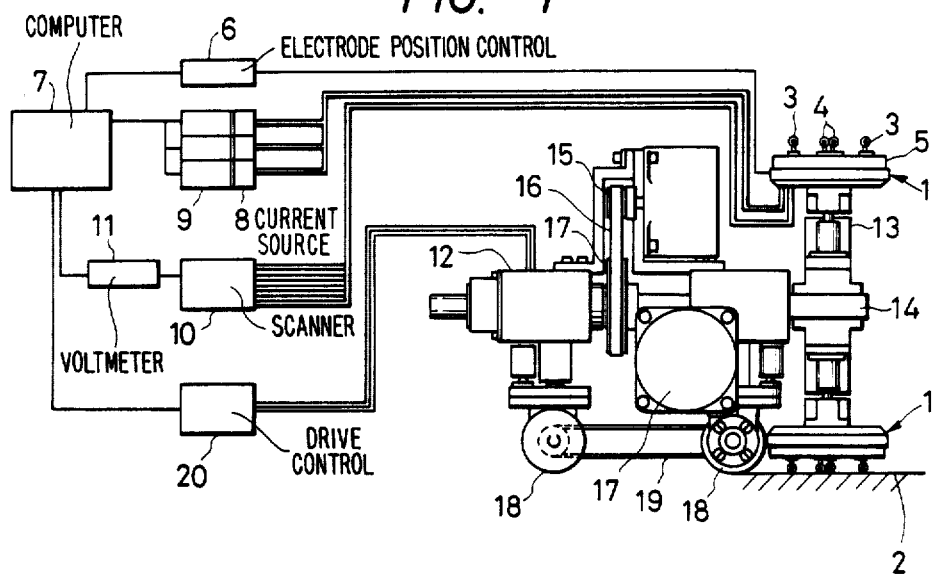
FIG. 1 is a diagram illustrating the whole structure of an apparatus according to the present invention.

FIG. 1 is a diagram illustrating the whole structure of an apparatus for inspecting surface defects according to the invention wherein reference numeral 1 denotes a sensor head which detects surface defects of a structural member 2. The sensor head 1 consists of a plurality pairs of power supplying electrodes 3 for supplying a constant current to the structural member 2, pairs of potential difference-measuring electrodes 4 for measuring the potential distribution on the inside of the pairs of power supplying electrodes 3, the potential distribution changing depending upon the presence or absence of defects in the surface or depending upon the shapes thereof, and a sensor jig 5 for holding these pairs of electrodes. At the time of measurement, the sensor head 1 is pressed onto the structural member 2.

The pairs of power supplying electrodes 3 held by the sensor jig 5 are permitted to undergo displacement in response to control signals from a electrode position control unit 6 which is connected to a computer 7 via an interface. The pairs of power supplying electrodes 3 are connected to a constant-current source 9 via a polarity inverter that removes the thermoelectromotive force. The constant-current source 9 is connected to the computer 7. The pair of potential difference-measuring electrodes 4 are connected to a very highly sensitive voltmeter 11 via a scanner 10 so as to measure potentials at many points. The voltmeter 11 is connected to the computer 7 via an interface to process the measured data.

As an electric current is supplied from the constant-current source 9 to the pair of power supplying electrodes 4 in response to an instruction from the computer 7, a current distribution is established on the inside of the pairs of electrodes 4 depending upon the arrangement of the pairs of electrodes. The current distribution is measured by the pairs of potential difference-measuring electrodes, and a measured potential difference signal is input to the computer 7 and is processed. On the basis of the processed result, the electrode position control unit 6 produces a control signal to move the pairs of power supplying electrodes so that the current distribution is nearly uniformalized on the measured region on the inside of the pairs of power supplying electrodes 3. In the foregoing was described a preparatory step for practically detecting the defects. Namely, the structural member without defects in the surface which is the same as the structural member to be measured is used as a standard member, or the shape of the structural member to be measured and the arrangement of power supplying electrodes, is analyzed as data by the computer. The latter method is very convenient since no standard member is required. After the preparatory step for nearly uniformalizing the current distribution is finished, the measured potential difference signal of the structural member being measured is input to the computer 7. Unlike that of the preparatory step, this signal is processed by a defect determining unit (not shown) in the computer 7 to determine the presence or absence of defects in the surface or to determine the shape thereof. The detected result is displayed on the output device (not shown).

The sensor head 1 is mounted on a drive unit 12 to scan the entire surface. In this embodiment, the drive unit is designed for measuring cracks in the inner surface of the pipe. The sensor head 1 is pushed onto the structural member by pushing means 13 such as an air cylinder. The sensor head 1 is supported by a rotary shaft 14 to scan the inner periphery of the pipe in the circumferential direction thereof. The rotary shaft 14 is turned by a motor 15, a belt 16 and a pulley 17. Movement in the axial direction of the pipe is accomplished by a motor 17, a roller 18 and a coupling belt 19. The drive unit 12 is controlled by a drive control unit 20 which is connected to the computer 7.

The computer 7 employs a 16-bit microcomputer system, and a printer and a 5-inch floppy disk are used as a device for producing the detected result and as a device for recording the detected result. A periphery interface adapter (PIA) is used as the drive control unit 20 and the electrode position control unit 6, and a GP-IB interface is used as the voltmeter 11 and the constant-current source 9, so that the signals are input to, or taken out from, the computer 7.

Figure 2:
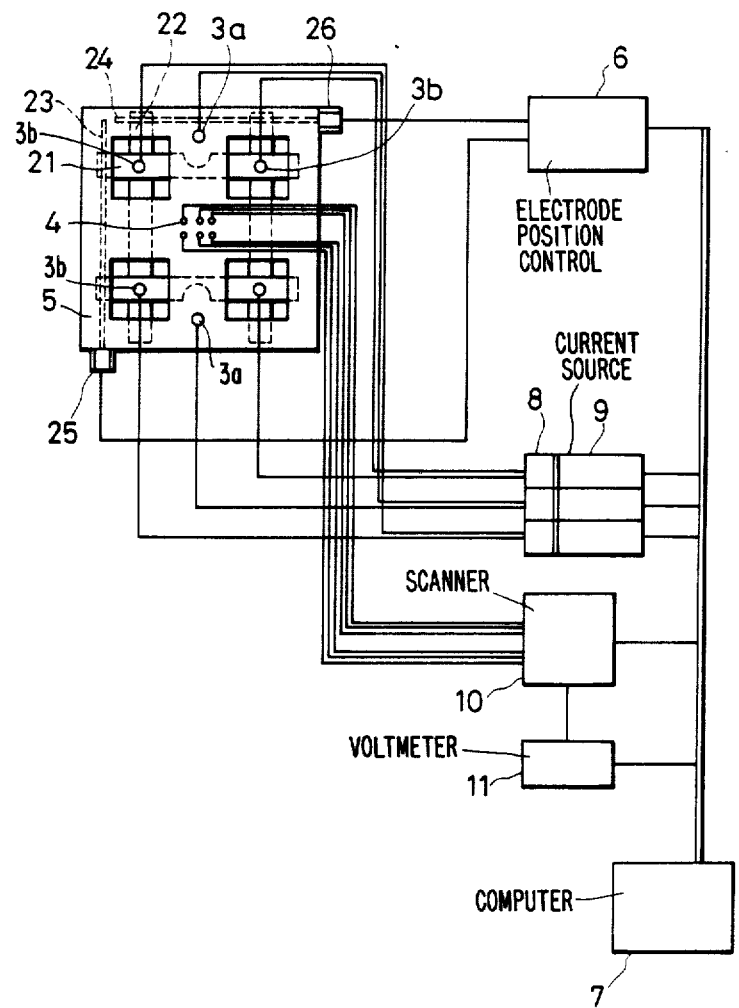
FIG. 2 is a plan view illustrating on an enlarged scale a sensor jig of FIG. 1.

FIG. 2 is a plan view illustrating on an enlarged scale a portion of the sensor jig of FIG. 1. The pairs of power supplying electrodes 3 have such a structure that among three pairs of terminals, the central pair of power supplying electrode 3a are fixed ones, and the other two pairs of power supplying electrode 3b on both sides are allowed to undergo displacement in the X-axis and Y-axis directions. That is, the pairs of movable power supplying electrodes 3b are made movable by levers 21 and 22, and threaded shafts 23 and 24 that screw into the levers 21 and 22, which are coupled together in a # form, and by motors 25 and 26 that turn the shafts 23 and 24. The motors 25 and 26 are controlled being connected to the electrode position control unit 6, and so operate that the power supplying electrodes will move to form an optimum arrangement as analyzed by the computer 7 so that a uniform current field is obtained. Here, all of the three pairs of power supplying electrodes may be made movable, as a matter of course.

Figure 3:
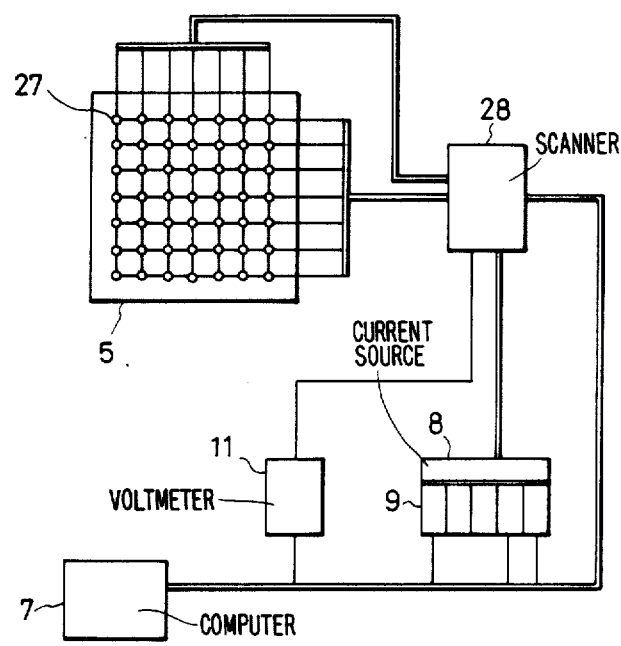
FIG. 3 is a plan view illustrating on an enlarged scale another embodiment according to the present invention.

FIG. 3 is a diagram illustrating the structure according to another embodiment of the invention, wherein a number of electrodes 27 are arranged in the form of a matrix on the sensor jig 5, and the pairs of power supply electrodes are, in effect, made movable by changing which of the terminals 27 that are selected out of the whole electrodes 27. The individual electrodes 27 have been fixed. However, if combinations of the power supplying are changed, the result is, in effect, a movement of the electrodes 27 which serve as the power supply electrodes. Part of the remaining electrodes 27 at the central ends constitute a pair of potential difference measuring electrodes. That is, the other ones of the individual electrodes 27 are connected to a matrix scanner 28, and the pairs of power supplying electrodes and the pair of potential difference measuring electrodes are arranged in an optimum way as analyzed by the computer 7. According to this embodiment, arrangement of the pairs of electrodes can be freely selected as either the power supply electrodes or the potential difference measuring electrodes, contributing to broadening the range of application and to simplifying the structure.

Figure 4:
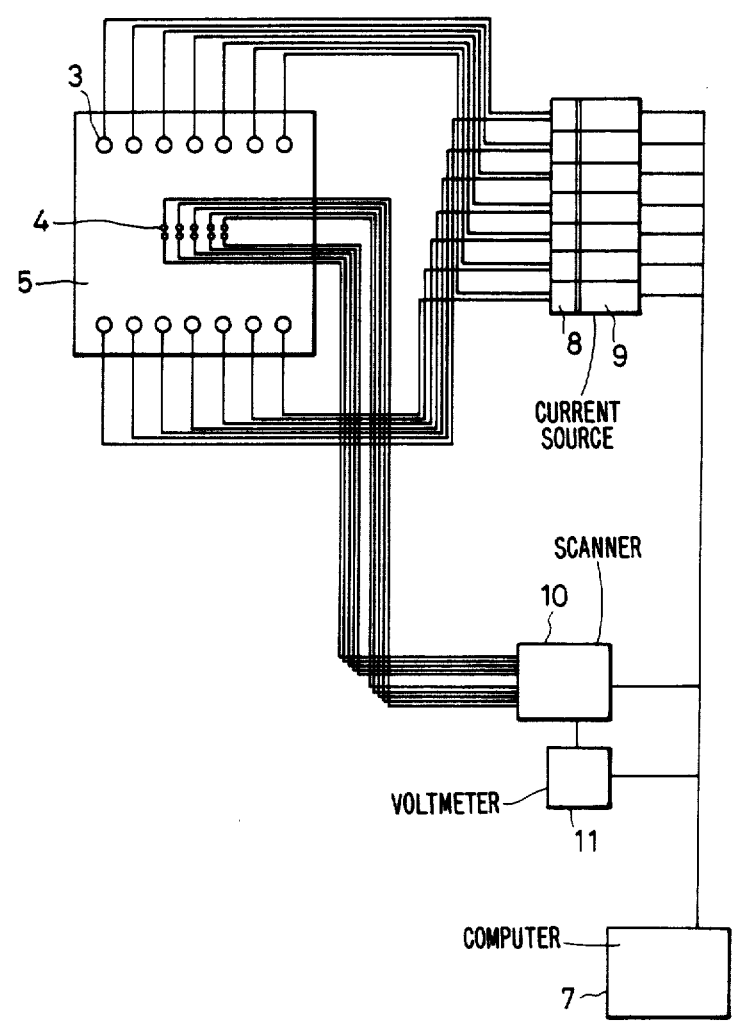
FIG. 4 is a plan view illustrating on an enlarged scale an embodiment of a further embodiment.

FIG. 4 is a diagram illustrating the structure of an embodiment of the second invention of claim 3. In this embodiment, there are seven pairs of power supplying electrodes that are not movable but are fixed unlike those of the first invention. The pairs of power supplying electrodes 3 are independently connected to the constant-current source 9 and receive currents that are individually controlled by control signals from the current control unit (not shown) contained in the computer 7. The current control unit detects, using the pairs of potential difference-measuring electrodes 4 like in the first invention, the current distribution established inside of the pairs of power supplying electrodes by the supplied current, and produces control signals based upon the measured signals so that a nearly uniform current distribution is obtained. Thus, a nearly uniform current field is formed on the measuring region, and the preparatory step enters into a post measurement step.

Figure 5:
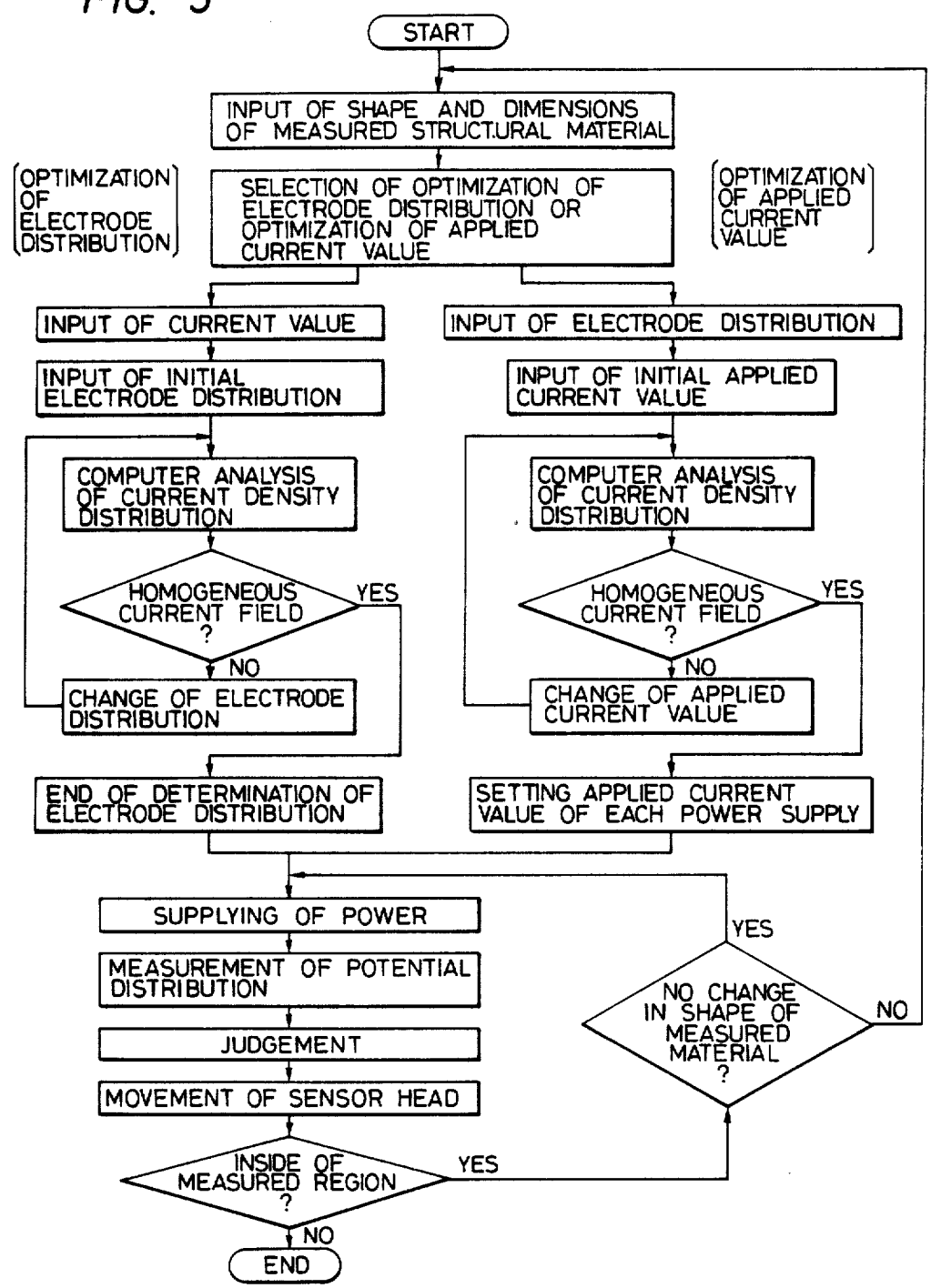
FIG. 5 is a diagram of a flow chart for detecting surface defects.

FIG. 5 shows a flow chart for detecting defects in the surface of a structural member using an apparatus according to the present invention. Either the first invention or the second invention can be adapted to the flow chart, and either of them can be selectively used. FIG. 5 does not illustrate the case where a uniform current field is formed in the preparatory step using a standard member, but illustrates the case where a uniform current field is formed in the preparatory step by the computer analysis by inputting data such as the shape of the structural member to be measured and the data related to current values and arrangement of the pairs of power supplying electrodes.

In a step 29 are input data of the shape of the measuring region of the structural member that is to be practically measured. This shape greatly affects the current distribution. Other factors that affect the current distribution are also input. A step selects an optimum arrangement of the pairs of power supplying electrodes. Usually, this selection is preferred. A step 31 inputs a current that is to be supplied to the pairs of power supplying electrodes 3. The current is the same for all pairs of the terminals 3. A step 32 inputs the data of initially set r arrangement of the pairs of power supply electrodes 3. This causes a current distribution to be established on the measuring region. The current distribution is analyzed by the computer in a step 33. That is, the current distribution is measured as a potential distribution by the pairs of potential difference-measuring electrodes 4, and the measured signals are input to the computer 7 to excute FEM analysis or a simple analysis in compliance with a logical equation. From the result of analysis, a step 34 determines whether the uniformity of the current distribution lies within the tolerable range or not. When it lies outside the tolerable range, a step 35 changes the data of arrangement of the pairs of power supplying electrodes 3, and the program returns back to the step 33 to analyze again the current distribution. The same procedure is repeated until a uniform current distribution is obtained that lies within the tolerable range. A step 36 ends the positioning of the pairs of power supplying electrodes 3 on the sensor jig 5.

A uniform current distribution is obtained through the above-mentioned preparatory step, and the defects in the surface are practically detected in a step 37 and in subsequent steps. In the step 37, first, a current same as the current input in the step 31 is supplied to the pairs of power supplying electrodes 3 whose position have been determined. A step scans the pairs of potential difference-measuring electrodes 4 to measure the potential distribution on the measuring region. On the basis of the measured potential difference signals, a defect determining unit determines in a step 39 the presence of absence of defects in the surface of a member and the shapes thereof. Here, if the potential distribution is uniform, it means that there exists no defect in the surface of the region. If there exists non-uniform portions such as peaks, it means that there exist defects in the surface of the structural member at the corresponding positions. Further, the shape of defect is determined in comparison with a master curve or the like that has been found in advance. After the determination, the sensor head 1 is moved to other measuring region by the drive unit 12 in the step 40. When there is no change in the data such as the shape of the measuring region of the structural member, the same procedure is repeated starting from the step 37. When there is a change in the shape or the like, the procedure is returned back to the step 29 from the step 41, and is carried out again from the first. The program ends when the sensor head 1 is positioned outside the measurable range.

The supply current is optimized in a following way.

The step 29 works in the same manner and the step 30 selects an optimum supply current. A step 42 inputs the data of arrangement of the pairs of power supplying electrodes 3. This arrangement is fixed. A step 43 inputs an initially set supply current. This causes a current distribution to be formed on the measuring region. The current distribution is analyzed by the computer in a step 44. The method of analysis is the same as the one described in connection with the first invention. When it is determined in a step 45 that the uniformity of the current distribution lies outside the tolerable range, a step 46 changes the supply current and whereby the program returns back to the step 44. The same procedure is, repeated until a uniform current distribution is obtained. At a step 47, the power sources are set to meet final currents that are supplied to the pairs of power supplying electrodes 3. The uniform current distribution is obtained through the above-mentioned preparatory step, and defects in the surface are detected through the same procedure as the one mentioned earlier in connection with the steps 37 and subsequent steps.

Principle of the invention will now be described.

The current field can be analyzed by using the finite element method. However, the flow of electric current in a uniform continuum corresponds to the electric charge and the line of electric force, and can be found by analysis. That is, the current density is substituted as a surface charge on the coordinate that is to be found, i.e., found in accordance with the following fundamental equations:

$$I \to q \quad (1)$$

$$V = \frac{q}{4\pi\epsilon_0}\left(\Sigma \frac{1}{r_i}\right) \quad (2)$$

$$ix_i \to \sigma x_i = -\epsilon_0 \left(\frac{\partial V}{\partial x_i}\right) \quad (3)$$

where,
I: electric current,
q: electric charge,
$x_i$: coordinate,
$ix_i$: current density of component $x_i$,
$\sigma x_i$: surface charge density of component $x_i$.

The current field can be easily analyzed by incorporating a program using these fundamental equations into the computer 7. The finite element method is used when the shape is particularly complex.

The result of analysis will now be described.

Figure 6A:
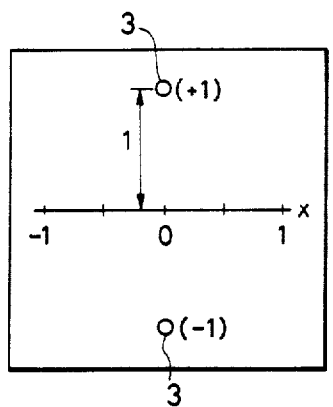
FIGS. 6(a) and 6(b) are diagrams of a current distribution that corresponds to an arrangement of a pair of power supplying electrodes.
Figure 6B:
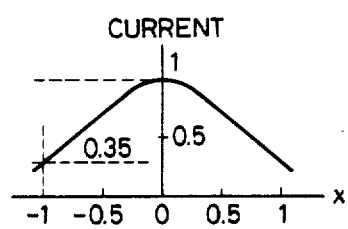

FIG. 6(a) is a diagram of the arrangement of a pair of power supplying electrodes 3 in a conventional four-terminal method, and FIG. 6(b) is a diagram of a current distribution on the inside of the pair of power supplying electrodes 3. If the magnitude of current at the center is 1, the current decreases to 35% at a position separated away from the center by a distance equal to one-half the distance between the pair of electrodes.

Figure 7A:
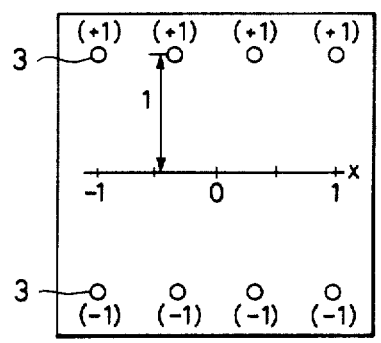
FIGS. 7(a) and 7(b) are diagrams of a current distribution that corresponds to a different arrangement.
Figure 7B:
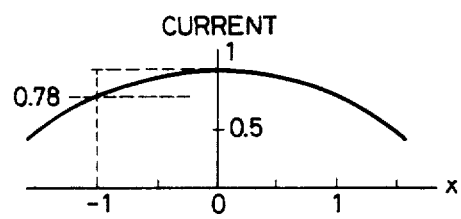

FIG. 7(a) is a diagram of the arrangement where four pairs power supply electrodes 3 are provided maintaining an equal distance relative to each other, and FIG. 7(b) is a diagram of a current distribution on the inside of the parts of electrodes 3 when the same current is supplied thereto. The current is maintained at 78% at a position separated away from the center by a distance equal to one-half the distance between the pair of electrodes.

Rearrangement of the results of FIGS. 6 and 7 is shown in FIG. 8 which illustrates a relationship between the number n of the pairs of power supplying electrodes and the current distribution. It will be comprehended that the current distribution is flattened when the electrodes are provided in a plurality of pairs compared with the conventional case where n=1, i.e., where only a pair of power supplying electrodes are provided. Interference among the electrodes is improved when n=4 or higher.

Figure 9A:
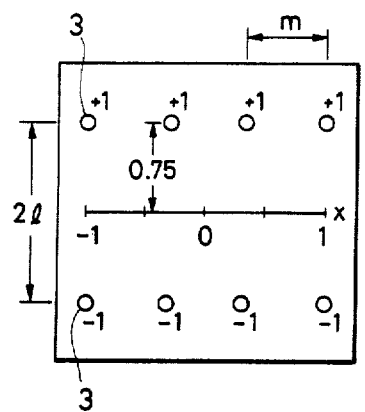
FIGS. 9(a) and 9(b) are diagrams of a current distribution that corresponds to an arrangement of pairs of power supplying electrodes.
Figure 9B:
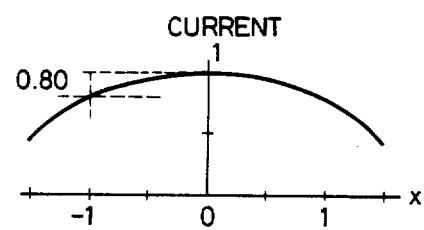
Figure 10A:
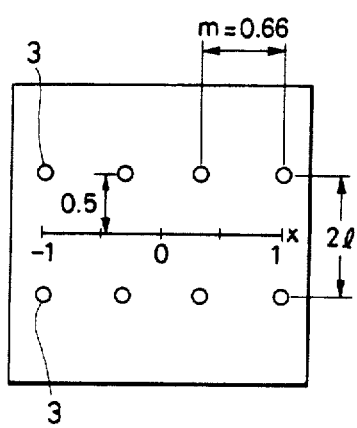
FIGS. 10(a) and 10(b) are diagrams of a current distribution that corresponds to an arrangement having a different distance l between the electrodes.
Figure 10B:
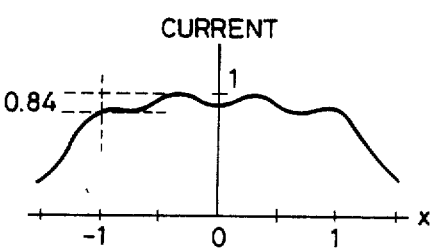
Figure 11A:
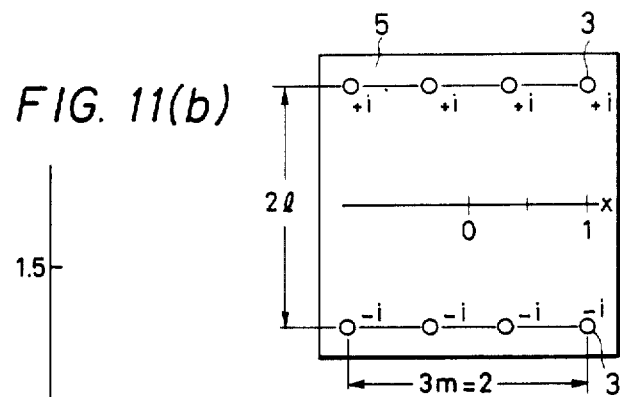
FIGS. 11(a) and 11(b) are diagrams illustrating a relationship between the current distribution and the distance l between the pairs of power supply electrodes.
Figure 11B:
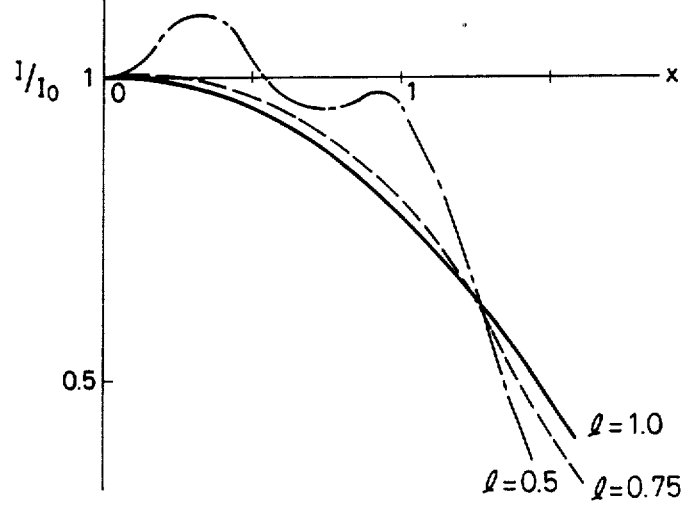

FIG. 9(a) is a diagram of the arrangement where a distance 2l between the pair of power supplying electrodes 3 is 1.5 (l=0.75 from the center), and FIG. 9(b) is a diagram which illustrates a corresponding current distributions. FIG. 10(a) is a diagram of the arrangement where the distance 2l between the pair of power supplying electrodes is 1.0 (l=0.5), and FIG. 10(b) is a diagram which illustrates a corresponding current distribution. The results of FIGS. 9 and 10 are arranged in FIG. 11. It will be comprehended that the uniformity in the current distribution is improved with the decrease in the distance l between the power supplying electrodes. However, if the distance l becomes too small, mutual interference decreases among the neighboring electrodes and the uniformity is deteriorated. This is determined by a relation of the neighboring distance m of the pairs of power supplying electrodes. It was confirmed through extensive experiments that the uniformity is poor when m>l.

Figure 12A:
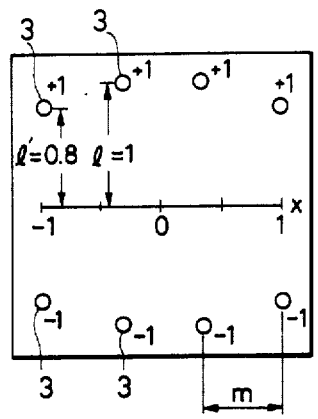
FIGS. 12(a) and 12(b) are diagrams of a current distribution that corresponds to an arrangement where the distance varies between the electrodes.
Figure 12B:
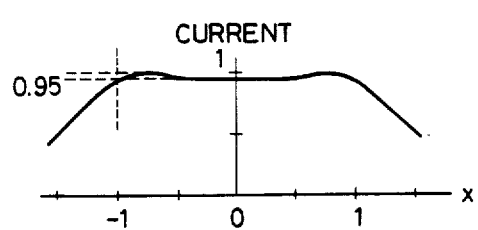
Figure 13A:
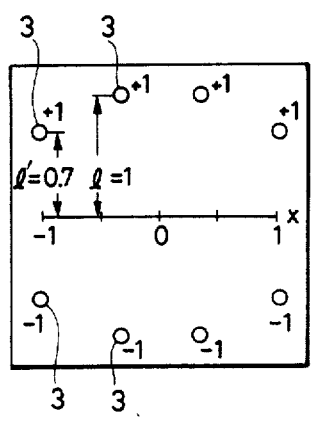
FIGS. 13(a) and 13(b) are diagrams of a current distribution that corresponds to a different arrangement.
Figure 13B:
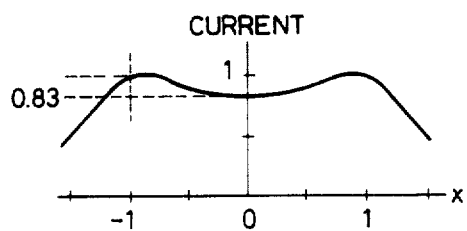
Figure 14A:
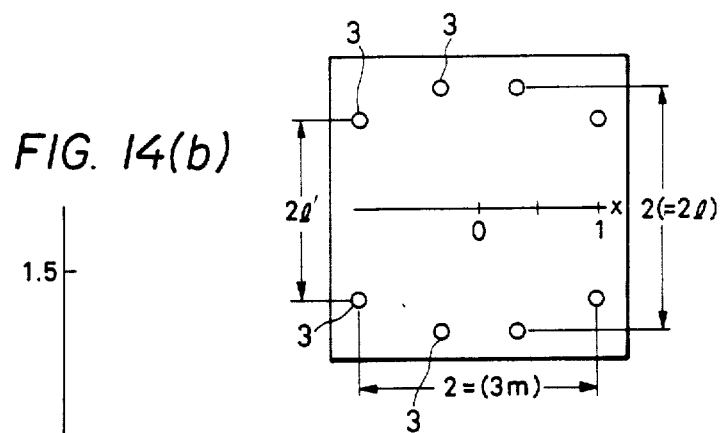
FIGS. 14(a) and 14(b) are diagrams illustrating a relationship between the current distribution and the degree of difference in the distance between the electrodes.
Figure 14B:
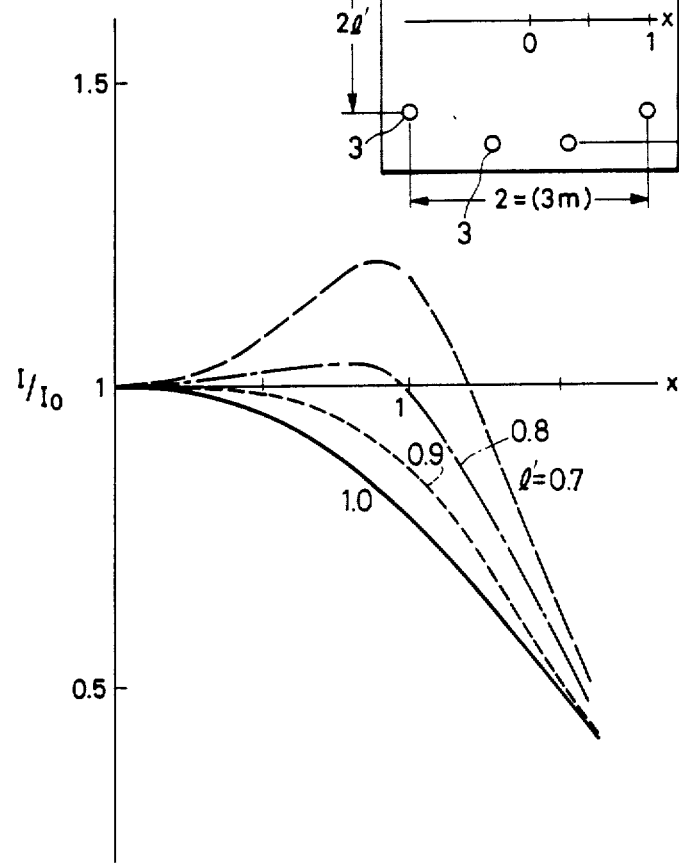

FIG. 12(a) is a diagram of the arrangement where a distance l' between the pairs of power supplying electrodes 3 is set to be smaller than the distance between the central pairs of electrodes 3, and FIG. 12(b) is a diagram which illustrates a corresponding current distribution. Here, the distance l is set to be 1 and the distance l' is set to be 0.8. FIG. 13(a) is a diagram of the arrangement where the distance l' is set to be 0.7, and FIG. 13(b) is a diagram which illustrates a current distribution. The results of FIGS. 12 and 13 are rearranged in FIG. 4. It will be understood that when l'=0.7, l=1.0 and m=0.66, the current distribution varies only by 5% over a range of $-1 \leq X \leq 1$ and remains nearly uniform (FIG. 12(b)). However, if the distance l' is too decreased, effect of the pairs of power supplying electrodes at the extreme ends becomes great which is detrimental to the uniformity (FIGS. 13 and 14). When there are provided four pairs of power supplying electrodes and 3m=2 and l=1, it will be recognized that the best uniformity is obtained with l'=0.8 to 0.9.

Figure 15A:
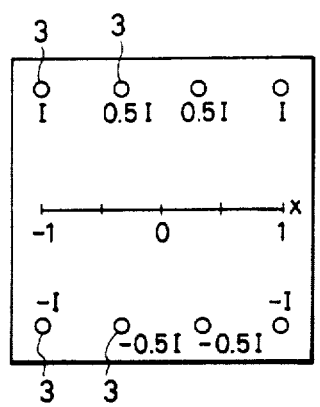
FIGS. 15(a) and 15(b) are diagrams of a current distribution which corresponds to an arrangement where different currents are supplied.
Figure 15B:
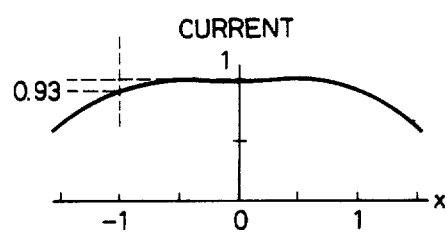
Figure 16A:
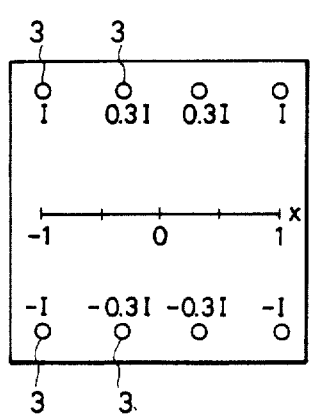
FIGS. 16(a) and 16(b) are diagrams of a current distribution that corresponds to an arrangement where different currents are supplied.
Figure 16B:
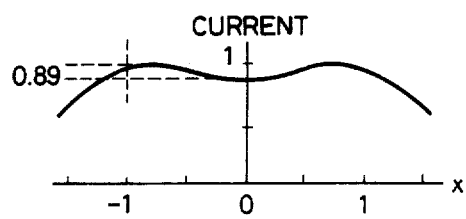
Figure 17A:
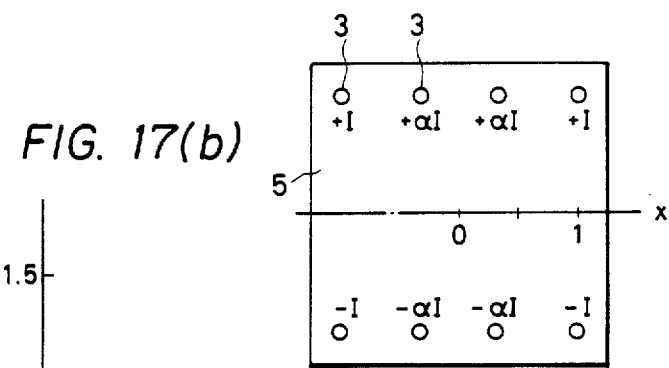
FIGS. 17(a) and 17(b) are diagrams illustrating a relationship between the current distribution and the degree of difference in the supply current.
Figure 17B:
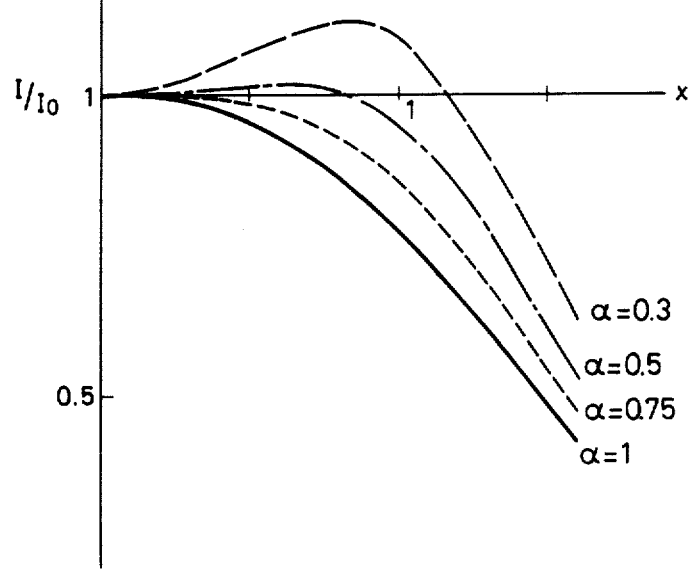

FIG. 15(a) is a diagram of the arrangement of the case where a current (0.5 I) supplied to the inner pairs of electrodes is set to be smaller than a current (I) that is supplied to the pairs of power supplying electrodes 3 on both sides, and FIG. 15(b) is a diagram illustrating a corresponding current distribution. FIG. 16(a) is a diagram of the arrangement of the case where a current supplied to the inner pairs of electrodes is further decreased (0.3 I), and FIG. 16(b) is a diagram which illustrates a corresponding current distribution. When the difference in the supplied current is 50% (FIG. 15), the current distribution varies by 7%. When the difference is 70% (FIG. 16), however, the current density decreases at the center and the current distribution loses uniformity. These results are summarized in FIG. 17.

As described above, the current distribution can be uniformalized by providing a plurality of pairs of power supplying electrodes 3 and by changing the arrangement of the pairs of electrodes, or by changing the current supplied to each of the pairs of electrodes. Based upon this principle, therefore, non-formity in the current distribution caused by the difference in the shape of the structural member is cancelled by changing the arrangement of the pairs of power supplying electrodes, to accomplished uniformity.

Figure 18:
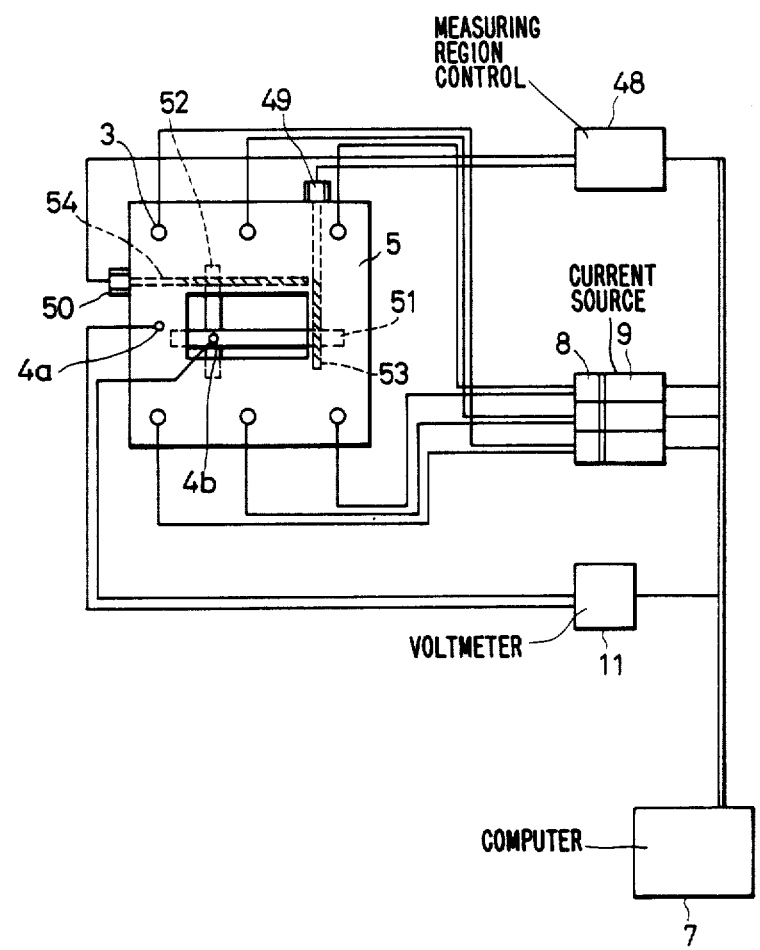
FIG. 18. is a plan view illustrating on an enlarged scale of a further embodiment of the invention.

FIG. 18 is a diagram of the structure of an embodiment of the third invention. There are provided three pairs of power supplying electrodes 3 that are fixed, and a fixed current is supplied thereto. Due to this arrangement and current, a current distribution is established inside of the pairs of power supplying electrodes 3. In the thus formed current distribution according to this invention, only a uniform region is determined to be a region that is to be measured and scanned by the pair of potential difference-measuring electrodes 4. That is, the pair of potential difference-measuring electrodes 4 are formed being allowed to undergo displacement. Here, one is a fixed electrode 4a and the other is a movable electrode 4b to simplify the structure. The movable electrode 4b scans a predetermined region responsive to control signals from a measuring region control unit 48 which finds a uniform region in the current distribution from the arrangement of the pairs of power supplying electrodes 3, current supplied and the shape of structural members relying upon the analysis using the computer 7 in the same manner as described earlier and produces control signals. The movable electrodes 4b is allowed to move in the X-axis and Y-axis directions owing to motors 49, 50, levers 51, 52 and threaded shafts 53, 54. The motors 49 and 50 are controlled being connected to the measuring region control unit 48 which is connected to the computer 7 via an interface. According to this aspect of the invention, only the region having a uniform current distribution is scanned by the pair of potential difference-measuring electrodes but the non-uniform regions are not scanned.

Figure 19:
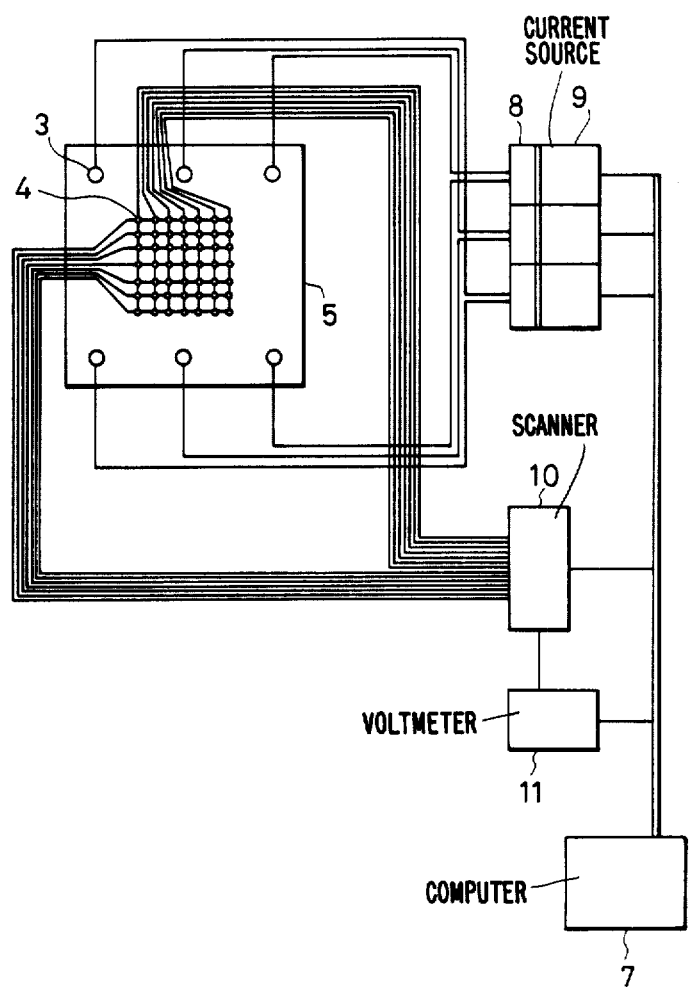
FIG. 19 is a plan view illustrating on an enlarged scale of yet another embodiment of the invention.
Figure 20:
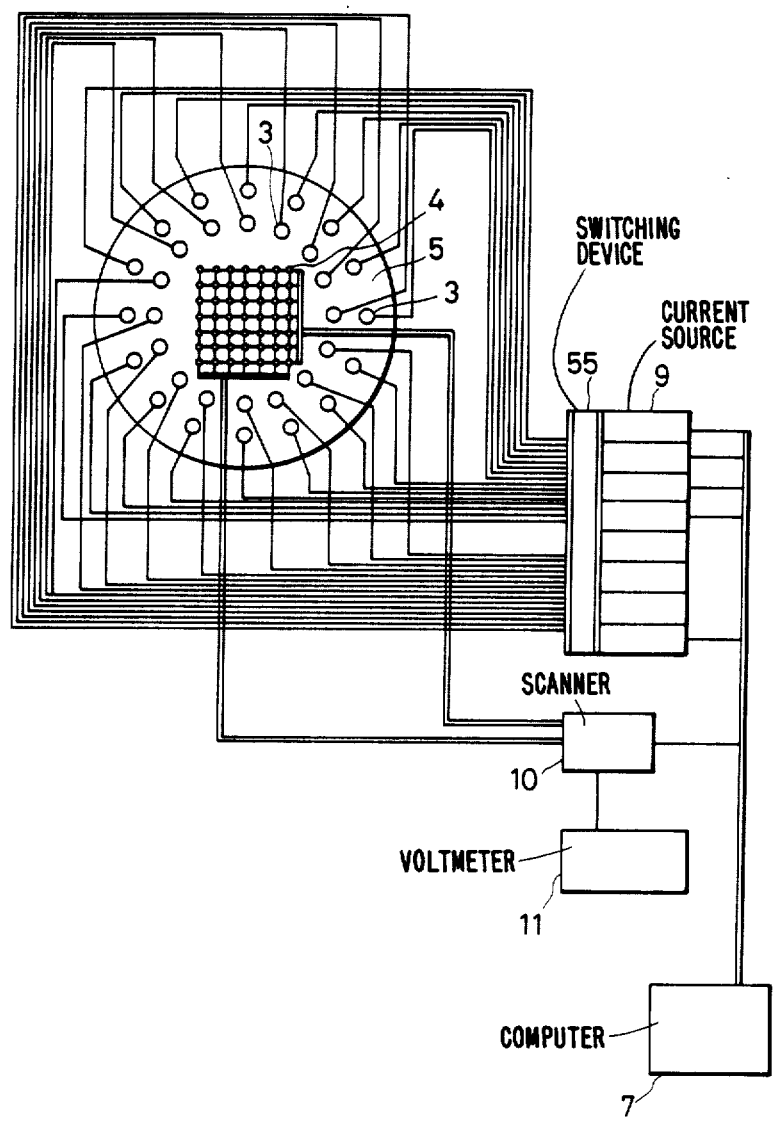
FIG. 20 is a plan view illustrating a further embodiment of the invention on an enlarged scale.

FIG. 19 illustrates another embodiment of the third invention wherein pairs of the potential difference-measuring electrodes 4 are arranged in the form of a matrix. According to this embodiment, the pairs of potential difference-measuring electrodes 4 are not directly moved but the electrodes to be used are suitably selected to facilitate the measurement. FIG. 20 illustrates a further embodiment wherein the pairs of power supplying electrodes 3 are arranged in the form of double concentric circles, the electrodes of the inner circle and the outer circle being served with currents of opposite polarities, i.e., being served with a current of positive polarity and a current of negative polarity. The pairs of power supplying electrodes 3 are connected to a constant-current source 9 via a switching device 55. According to this embodiment, the electric current is not supplied to all of the pairs of power supplying electrodes 3 but is supplied to only some of the electrodes of the inner and outer circles to generate a uniform current distribution. The switching device 55 is provided to select or exchange the electrodes to which the current is to be supplied. After a uniform current field is obtained, a rotary current field is formed by switching the supply of current on the whole electrodes while maintaining the arrangement of the electrodes served with the current and maintaining the current value. The pairs of potential difference-measuring electrodes are provide in the form of a matrix to follow the rotary current field in synchronism therewith. According to this embodiment in which currents of opposite polarities are supplied to the pairs of power supplying electrodes 3 of the inner and outer circles, no current leaks out of the measuring region, and the measurement is little affected by adjacent defects or by the change in the shape of structural members.

Figure 21A:
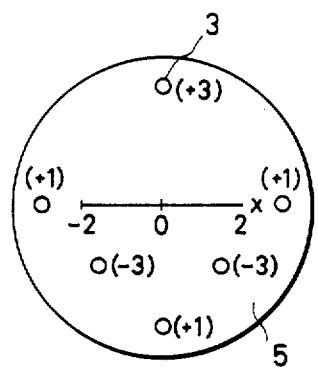
FIGS. 21(a) and 21(b) are diagrams of a current distribution that corresponds to an arrangement of electrodes.
Figure 21B:
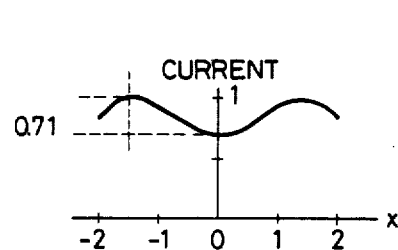
Figure 22A:
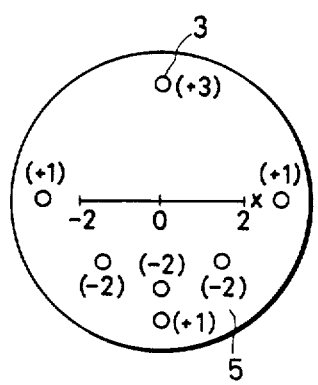
FIGS. 22(a) and 22(b) are diagrams of a current distribution that corresponds to a different arrangement of electrodes.
Figure 22B:
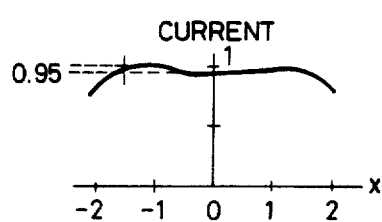

The principle of this embodiment will now be described. FIG. 21(a) is a diagram of an arrangement showing the current values to be supplied and the electrode positions, and FIG. 21(b) is a diagram showing a corresponding current distribution. FIG. 22(a) is a diagram of arrangement where the number of electrodes of the inner periphery is increased to three, and FIG. 22(b) is a diagram showing a corresponding current distribution. It will be understood that the arrangement of FIG. 22(a) makes it possible to obtain a uniform current distribution. A uniform rotary current field is obtained by switching the electrodes to be used by the switching device 55 under this condition. Tilted cracks in the structural member can be easily detected owing to the rotary current field without moving the sensor head 1.

According to one feature of the invention, non-uniformity in the current distribution caused by the shape and the like of the measuring region of the structural member is cancelled by moving the pairs of power supplying electrodes by the electrode position control unit in a direction to cancel the non-uniformity in order to obtain a uniform current distribution without affected by the shape or the like. Therefore, presence or absence of defects in the surface and the shapes of defects can precisely be detected making it possible to observe the progress of defects maintaining high precision.

According to the another feature of the invention, the currents supplied to each of a plurality of pairs of power supplying electrodes are individually controlled by the current control unit to uniformalize the current distribution, making it possible to obtain the same effects as those of the first invention.

According to a further feature of the invention, the region to be measured and scanned by the pairs of potential difference-measuring electrodes is determined base upon the current distribution and the region having uniform distribution is scanned to detect defects in the surface maintaining high precision.

Figure 23:
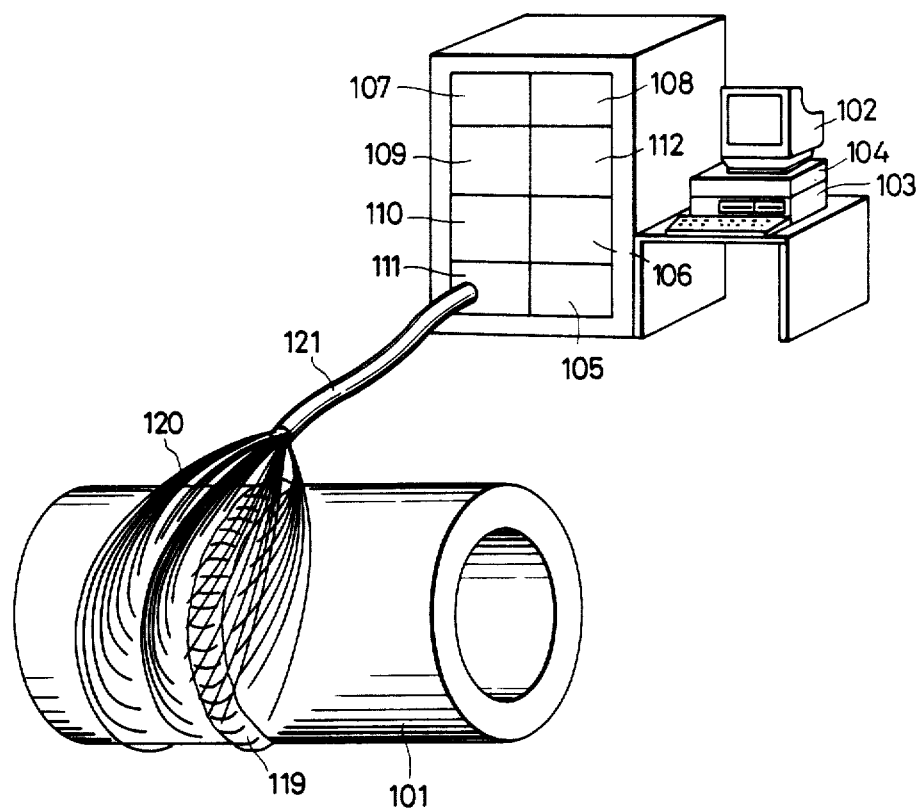
FIG. 23 is a diagram showing the appearance of an illustrative apparatus for monitoring cracks in a conduit.
Figure 24:
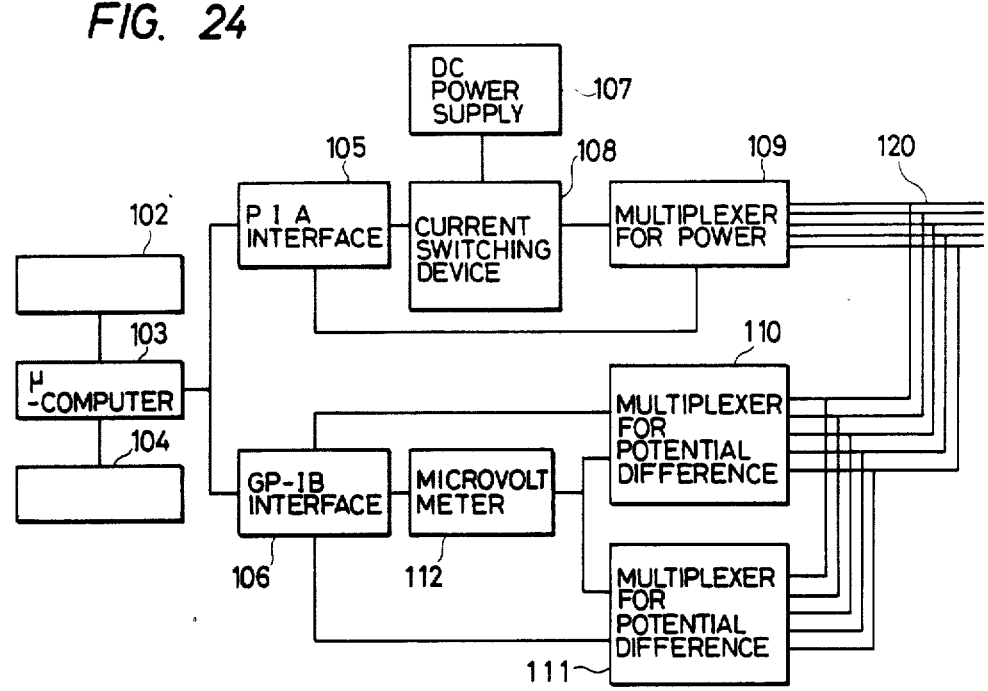
FIG. 24 is a system diagram of the crack monitoring apparatus of FIG. 23.

FIG. 23 illustrates an apparatus for monitoring cracks in a conduit and FIG. 24 is a diagram showing a control/measurement/calculation system in an apparatus for monitoring cracks in the conduit. Reference numeral 103 denotes a computer, 104 denotes an external extra memory such as a hard disk for storing data and programs, and 102 denotes a CRT. The computer 103 controls the measuring apparatus via an interface 105 and a GP-IB interface 106, and process the measured values that are received, and produces the result. In FIG. 23, electrodes 120 that work to supply DC currents and to measure potential difference are spot-welded onto a conduit 101 near a welded portion 119 maintaining an equal distance in both axial direction and the circumferential direction. The electrodes 120 are usually composed of SUS 304, SUS 316 or nickel having resistance against oxidation. Though not illustrated in FIG. 23, the electrodes 120 run through a path provided inside a heat insulating material, go out of the heat insulating material, and are connected to the measuring apparatus being sheathed in a cable 121. In this case, the electrodes 120 must have been insulated from each other and from the conduit 101; i.e., the electrodes 120 must be extended passing through short insulator tubes or being covered with an insulating material. The electrodes 120 may be bundled together on the outside of the heat insulating material and may be contained in a cable. However, since the temperature is low on the outside of the heat insulating material, the electrodes are better connected to an ordinary multicore cable. The electrodes 120 are all connected to three multiplexers, i.e., to a multiplexer 109 for switching the power supplying electrodes and to two multiplexers 110 and 111 for switching the potential difference-measuring electrodes.

DC currents supplied from a plurality of stabilized DC power supply 107 are changed for their polarities by a current switching device 108 that is controlled by the computer 103 via the interface 105, supplied to the multiplexer 109, and are supplied to particular electrodes 120. One or two multiplexers 110 and 111 switch the electrodes of measurement, and potential differences among many electrodes 120 are connected to a very sensitive potentiometer 112 and are measured. The measured potential differences are transferred to the computer 103 via GP-IB interface 106. The computer 103 determines the shape of crack from the potential difference distribution in the axial direction and circumferential direction of the conduit relying upon a method that will be described later. Here, the multiplexers 109, 110, 111 and the very sensitive potentiometer 112 are controlled by the computer 103 via GP-IB interface 106 or interface 105.

Figure 25:
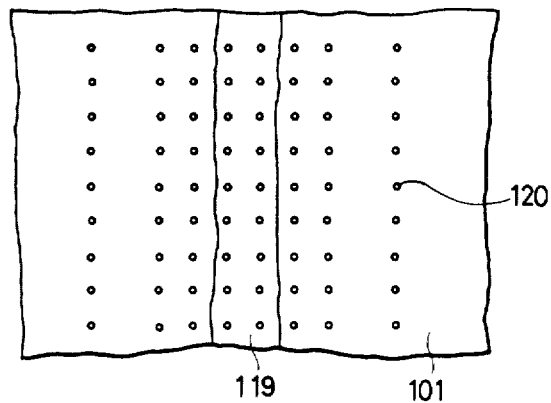
FIGS. 25 and 26 are diagrams illustrating the electrode arrangement of the apparatus of FIG. 23.
Figure 26:
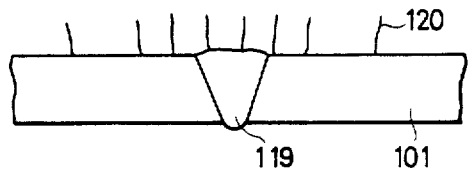

FIG. 25 is an expression plan of the arrangement of terminals 120 on the outer surface of the conduit, and FIG. 26 is a section view thereof in the axial direction. Generally, defects in the nuclear power plant and chemical plant stem from stress corrosion cracking and corrosion fatigue. The stress corrosion cracking is initiated in the places where there exists tensile residual stress near the welded portion and the corrosion fatigue is initiated in the root portions of the welded metals where there exists residual stress and the shape is discontinuous. Because of these reasons, the electrodes 120 are arranged near the welded portion. The stress corrosion cracking is initiated in the circumferential direction of weld heat affected zone and rarely is initiated being tilted with respect to the circumferential direction. In detecting the shape of defects by the potential method in accordance with the fourth invention, it is essential to apply an electric field perpendicular to the defects and to measure the potential difference distribution with the defects sandwitched therebetween. When the potential difference distribution is measured by the on-line method while fixing the electrodes, however, it is quite impossible to estimate in which direction the cracks will be inititated. Therefore, the electrodes 120 must be so arranged as will be able to measure the potential difference distribution both in the circumferential direction and the axial direction. One of the method is represented by the electrode arrangement shown in FIGS. 25 and 26. As described earlier, cracks are initiated at weld heat affected zone. Therefore, the electrodes 120 are arranged to cover this regions maintaining an equal spacing in the axial direction. Likewise, the electrodes 120 are also arranged on the whole circumfeence in the circumferential direction maintaining an equal spacing. That is the electrods 120 are arranged in the form of a matrix. In the arrangement in the axial direction, in this case, the electrodes at both ends are used only as power supplying electrodes. In order to take measurement under the homogeneous electric field condition, therefore, it is better that these electrodes are installed maintaining a distance greater than the thickness of conduit from the neighboring electrodes.

In FIG. 26, electrodes 120 are arranged even on a welded metal 119. The electrodes, however, may not be arranged here since no crack is initiated in the welded metal 119. In the nuclear power plants, the conduits are continuously used without being repaired when cracks are small that are found using ultrasonic testing at the time of in-service inspection. Progress of cracks can be estimted by the method of fracture mechanics. Though the cracks will not grow too fast, when it is desired to monitor the cracks according to the method of the invention to assure higher safety, the electrodes 120 should be arranged only in the vicinities of the cracks.

Figure 27:
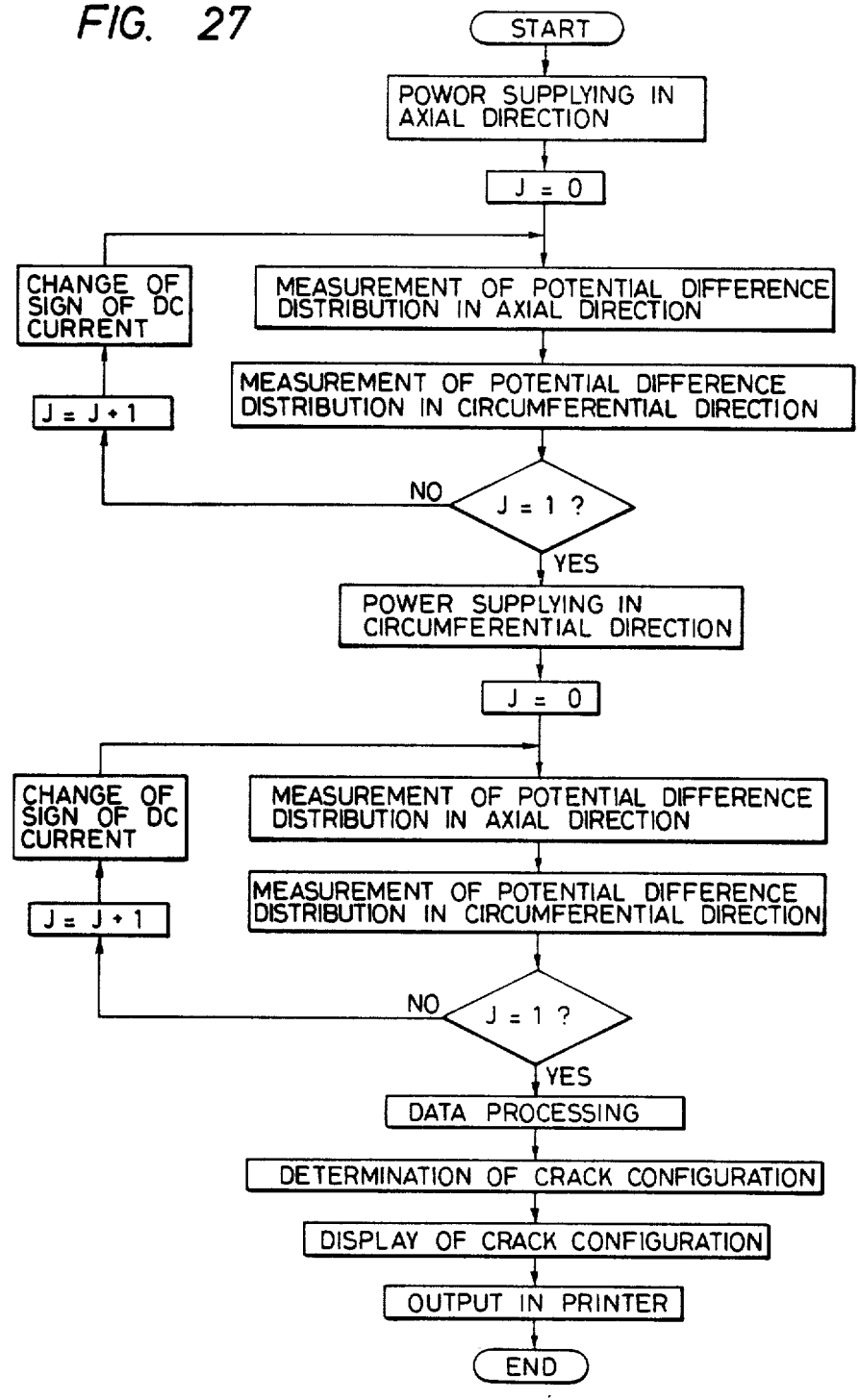
FIG. 27 is a diagram of flow chart for measuring the potential difference distribution according to the apparatus of FIGS. 23 and 24.
Figure 28:
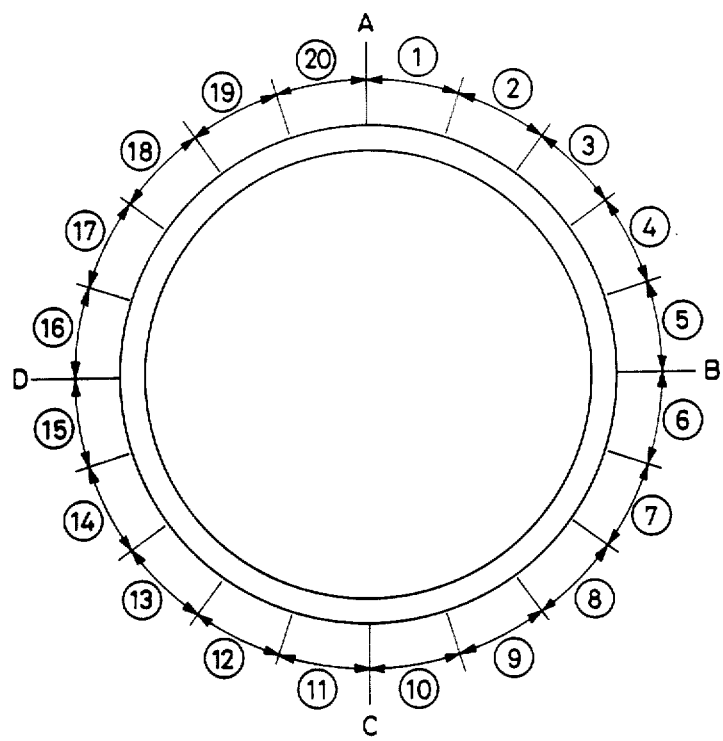
FIG. 28 is a diagram which illustrates power supplying electrodes and measuring electrodes of the case when the potential difference distribution is measured in the circumferential direction.

FIG. 27 is a flow chart for measuring the potential difference distribution. First, the multiplexer 109 is controlled to supply a direct current to feed-only electrodes at both ends of the conduit in the axial direction in order to form an electric field in the axial direction of the conduit. Next, potential differences are measured among a number of electrodes. Potential differences among the elctrodes that are neighboring to each other in the axial direction are measured by switching the electrodes by the multiplexers 110 and 111. (Next, potential differences are measured among the electrodes that are neighboring to each other in the circumferential direction.) After the potential difference is measured one time in the axial direction (and in the circumferential direction,) the polarity of the direct current is switched by the current switching device 108 and the potential difference is measured again in the axial direction (and in the circumferentail direction.) Next, an electric field is formed in the circumferential direction by switching the multiplexer 109 that feeds electric power. For instance, FIG. 28 illustrates the arrangement of electrodes on the section in the circumferential direction. First, a direct current is supplied form terminals A and C that are opposed to each other maintaining an angle of 180 degrees. Near the power supplying electrodes, the potential drops so drastically that the electric field is not maintained homogeneous and measurement of potential difference makes no sense. Therefore, potential differences are measured among, for example, the elecodes 3, 4, 5, 6, 7, 8, 13, 14, 15, 16, 17, 18 as shown in FIG. 28. Next, to measure the potential difference near the two electrodes A and C, a direct current is supplied to the lectrodes B and D that are separated by 90 degrees from the electrodes A and C, thereby to measure potential differences among the electrodes 1, 2, 9, 10, 11, 12, 19, 20. Even in this case, polarity of the supplied direct current is changed; i.e., the potential difference is evaluated based upon the amplitudes measured twice by supplying the current of positive polarity and the current of negative polarity. By switching the power supplying electrodes as described above, the potential difference distribution can be measured on the whole circumference under the homogeneous electric field condition. The measured potential differences are transferred to the computer 103 via the GP-IB interface 106 and are processed. The shape of crack is determined based on the measured result of potential difference distribution, the thus determined shape of crack is displayed on the CRT of the computer 103, and the printer produces the list output of result and a hard copy of the shape of crack.

In the foregoing was described the reasons for supplying a current in two directions, i.e., in the axial direction and in the circumferential direction. Details thereof will now be described. It is now presumed that a crack is in parallel with the axial direction of the conduit. In this case, even if a current is permitted to flow in the axial direction, the electric field which is oriented in the axial direction is not disturbed by the crack. Namely, the potential difference distribution that is measured is quite the same as that of when there is no crack, and it is determined that there is no crack. However, if a current is permitted to flow in the circumferential direction with respect to the crack in the axial direction of the conduit, the electric field in the circumferential direction is greatly distrubed by the crack whereby there is formed a potential difference distribution from which the size of crack can be determined. When the crack is tilted relative to both the axial direction and the circumferential direction of conduit, the shape inclusive of its inclination can be determined from the potential difference distribution that is measured by supplying a current in two directions.

Figure 29:
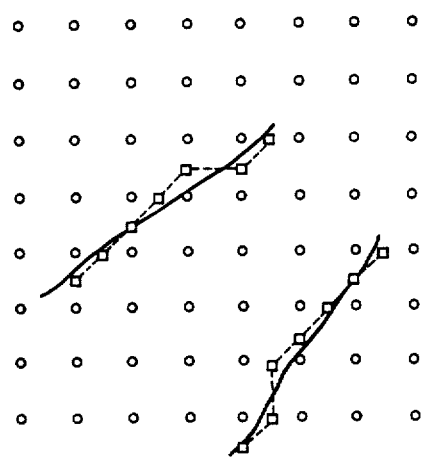
FIG. 29 is a diagram illustrating a method of determining the crack position using the apparatus of FIGS. 23 and 24.

With the current supplying in the axial direction, if there is no crack in the conduit, the potential difference to be measured remains constant across the terminals in the axial direction and the potential difference is zero across the electrodes in the circumferential direction. If a crack is initiated in the circumferential direction, the electric current flows detouring around the timp of crack and the current density increases on the outer side of the conduit so that the potential difference across the electrodes in the axial direction with the crack sandwitched therebetween becomes greater than the potential difference across the electrodes between which no crack is sandwitched. At the same time, a potential distribution develops in a direction in parallel with the crack and the potential difference across electrodes in the circumferential direction becomes greater than zero. The potential difference of a region where there exists no crack is regarded to be a reference potential difference, and it is determined that crack exists between the electrodes when the potential difference ratio is greater than 1.0 thereacross, making it possible to determine the position and shape of crack from the potential difference distribution. It is further determined that there exists crack between the elctrodes nearly in parallel therewith when the potential difference thereacross in the circumferential direction is greater than zero. In comparison with the potential difference across the neighboring electrodes in the axial direction, it is determined that there exists crack on the downstream side if the potential difference is great across the electrodes in the circumferential direction on the upstream side and it is determined that there exists crack on the upstream side if the potential difference is great across the electrodes on the downstream side. When the crack is tilted relative to the axial direction, it is determined that crack exists at a place at the center across the electrodes between which the potential difference ratio is greater than 1. FIG. 29 shows a method of determining crack position. In FIG. 29, open circles represent positions of electrodes 120 and solid lines represent crack positions. If the potential difference distribution is measured by applying an electric field in the axial direction, the potential difference becomes the greatest across the electrodes between which crack is sandwitched. It is not obvious where the crack exists between the electrodes. If it is presumed that the crack exists at the center between the electrodes, then the positions to be found are as marked with squares. Next, by applying an electric field in the circumferential direction, it is determined that cracks are located at positions marked with rhombuses. Broken lines represent coupled results of the positions marked with squares and rhombuses. Though FIG. 29 illustrates two examples, the practically found crack positions are nearly in agreement with the crack positions that are determined from the potential difference distribution.

Figure 30:
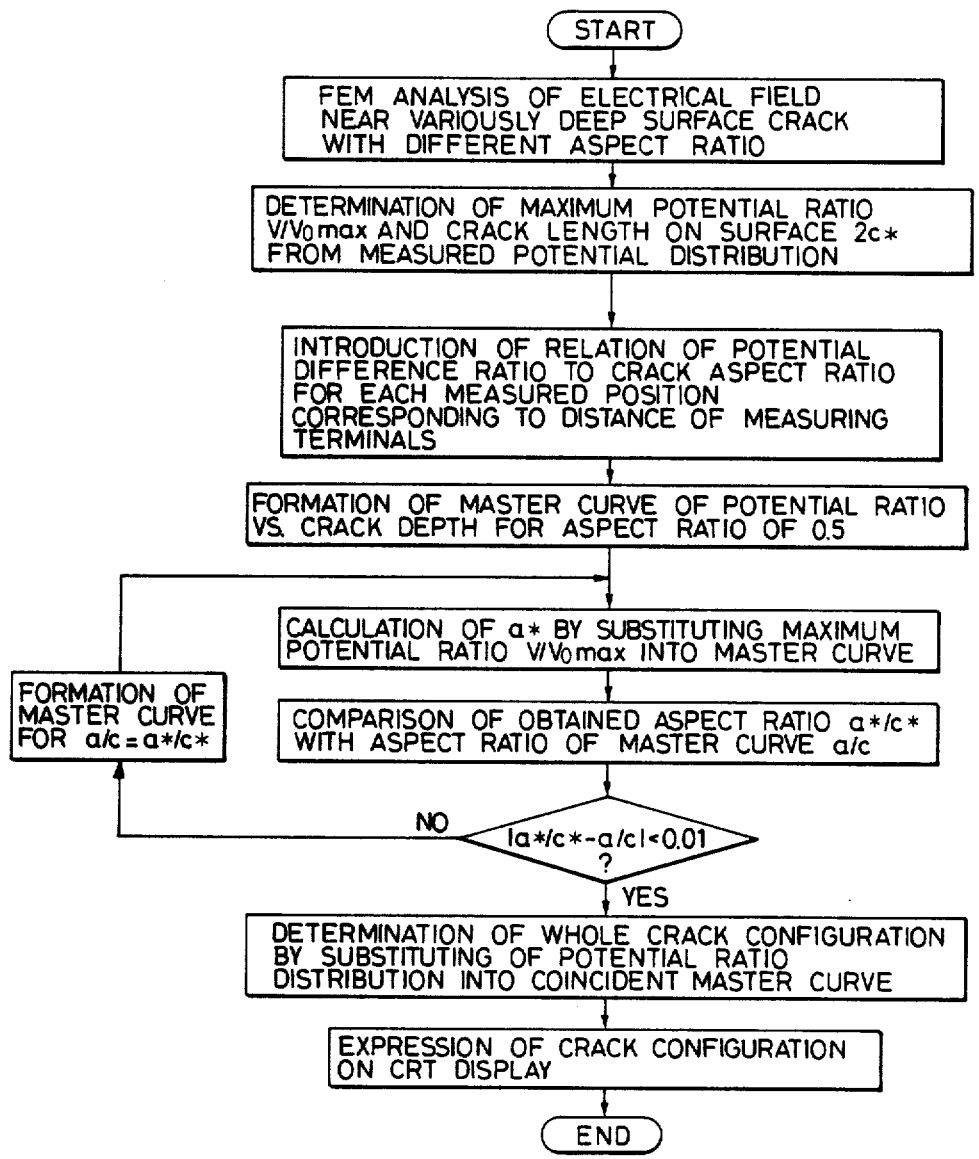
FIG. 30 is a diagram of flow chart for determining the crack shape using the apparatus of FIGS. 23 and 24.
Figure 31:
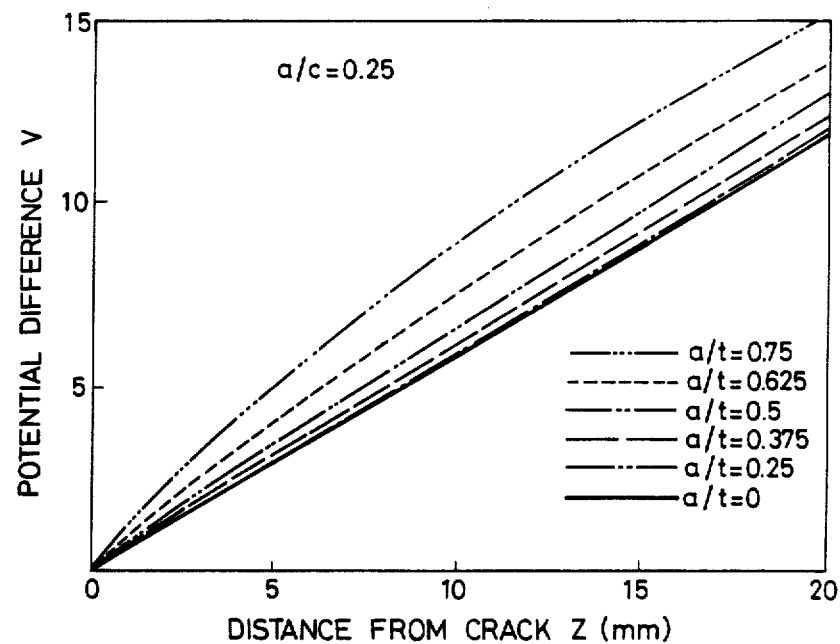
FIG. 31 is a graph showing potential difference distributions on the surface of the side opposite to the crack in a member as obtained by FEM using the apparatus of FIGS. 23 and 24.

Described below is how to determine the shape of crack from the potential difference distribution along the crack. FIG. 30 shows a flow chart for detemining the shape of crack in the surface. Using a large main frame computer, the electric field is analyzed in advance for a crack having various aspect ratios, e.g., $a/c=1.0, 0.5, 0.25, 0.1$, and a potential difference distribution in a direction perpendicular to the crack in the surface on the side opposite to the crack is stored in the memory 104. FIG. 31 shows potential difference distributions for cracks having different depths and having the aspect ratios $a/c=0.5$, that are to be stored. FIG. 30 is obtained by analyzing the elctric field relying upon FEM in the case where there exists a crack at the center of a flat plate having a thickness $t=20$ mm. Depths $a/t$ of cracks normalyzed with the plate thickness t are 0, 0.125, 0.25, 0.375, 0.5, 0.625 and 0.75 at the deepest points at the centers of cracks. When there is no crack ($a/5=0$), the potential difference varies in proportion to the distance z from the crack. When there exists crack, on the other hand, the potential difference gradually increases as the electrodes separate away from the crack and the increment of potential difference becomes nearly constant when the electrodes are separated away therefrom by a certain distance. These potential difference distributions are n-th approximated by n-th power equation and are stored in the computer 103 or in the external extra memory 4. In determining the shape of crack, the length $2c^*$ of crack in the surface and a maximum potential difference ratio $V/V_0max$ are found from the potential difference distribution around the crack measured for the first time.

Figure 32:
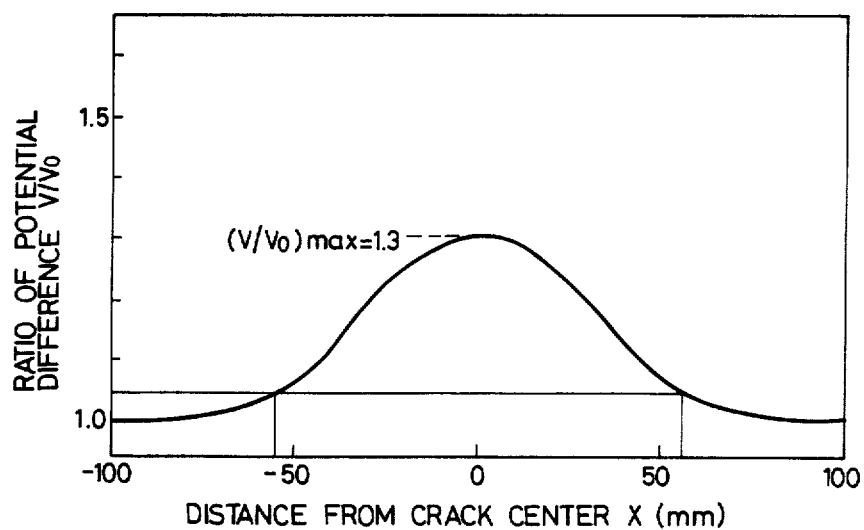
FIG. 32 is a graph showing a potential difference distribution around the crack on the surface of the side opposite to the crack in the member as obtained by FEM using the apparatus of FIGS. 23 and 24.

FIG. 32 illustrates a distribution of potential difference ratios around the crack obtained by analyzing the elctric field relying upon FEM. The aspect ratio of crack is $a/c = 0.25$, and a maximum depth of crack is $a = 12.5$ mm ($a/t = 0.625$). The potential difference is nearly constant in the areas where there exists no crack, and the distribution of potential difference ratios is indicated with the potential difference of such regions as a reference potential difference. The potential difference increases in a region where there exists crack, and the potential difference distribution of this region is subjected to approximation of n-th power equation. A maximum potential difference ratio $V/V_0max$ corresponding to the deepest point of crack is determined from a curve of approximation. In the case of FIG. 32, $V/V_0max = 1.30$ is obtained. In the potential difference distribution on the surface of the side opposiet to the crack, the potential difference gradually increases near the tip of crack which makes it difficult to specify the tip of crack. A relationship between the potential difference distribution and the tip position of crack was examined for a crack having various aspect ratios, and it was found that the tip of crack exists at around 0.15 of the peak of the maximum potential difference ratio $V/V_0max$. In FIG. 32, $V/V_0max = 1.30$. Therefore, if the length $2c^*$ of crack in the surface is found from a point of intersection of $V/V_0 = 1 + 0.3 \times 0.15 = 1.045$ and a curve approximated by fourth power equation curve, there is obtained $2c = 110$ mm.

Figure 33:
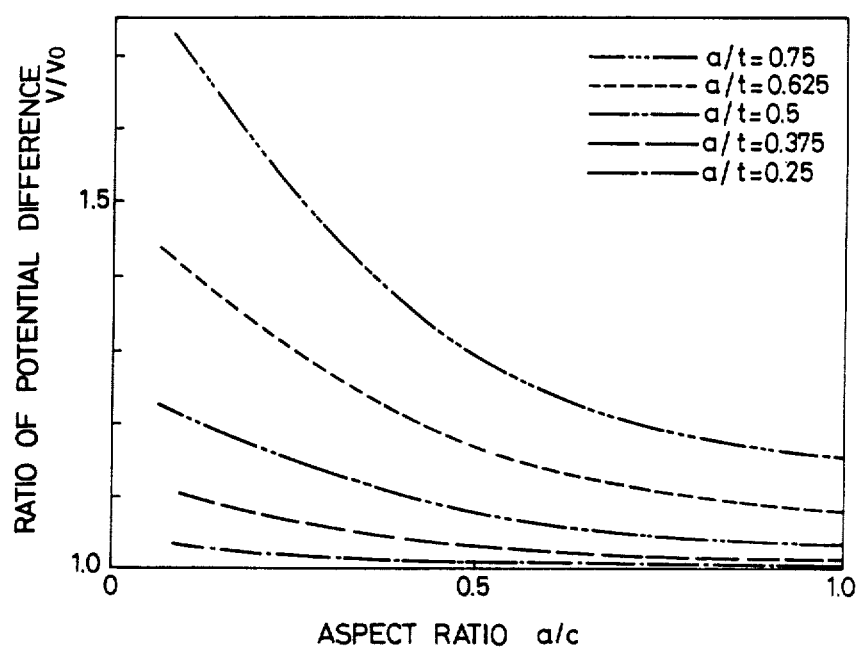
FIG. 33 is a graph showing relationships between the potential difference ratio and the aspect ratio using the apparatus of FIGS. 23 and 24.
Figure 34:
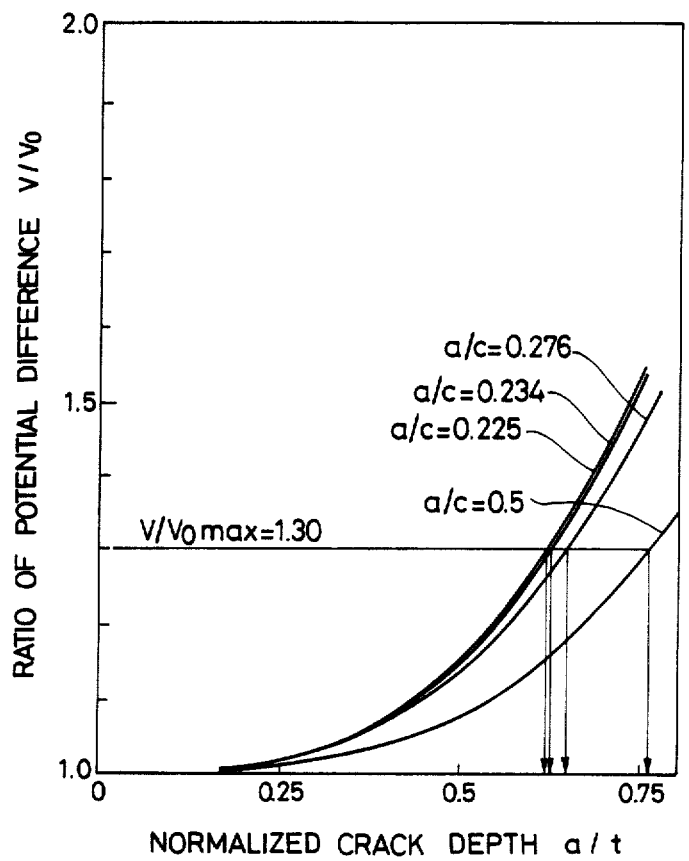
FIG. 34 is a graph showing relationships between the potential difference ratio and the depth of crack using the apparatus of FIGS. 23 and 24.

Next, a relationship between the potential difference ratio $V/V_0$ and the aspect ratio $a/c$ is prepared from the potential difference distributions shown in FIG. 31 in order to obtain a relationship between the depth of crack $a/t$ and the potential difference ratio $V/V_0$ for the crack of various aspect ratios $a/c$. In this case, the electric field is analyzed relying upon FEM using a flat plate having a thickness $t = 20$ mm, and a relation between the potential difference ratio $V/V_0$ and the aspect ratio $a/c$ must be prepared at a measuring position $d^*$ that corresponds to a distance $d$ between the measuring electrodes. For this purpose, potential difference is found for a depth $a/t$ of crack at a position $d^* = d \times 20/t^*$ corrected by the thickness $t^*$ of the material to be meausred, in order to obtain a relationship between the potential difference ratio $V/V_0$ and the aspect ratio $a/c$ as shown in FIG. 33. The relationship between the potential difference ratio $V/V_0$ and the aspect ratio $a/c$ is subject to approximation of n-th power equation for every depth $a/t$ of crack and is stored in the memory 104 in the computer 103. Next, using a relationship between the potential difference ratio $V/V_0$ and the aspect ratio $a/c$, master curves are obtained as shown in FIG. 34 to represent relationships between the depth $a/t$ of cracks and the potential difference ratio $V/V_0$ for the aspect ratio $a/c = 0.5$. Even in this case, the relationship between the potential difference ratio $V/V_0$ and the depth $a/t$ of crack is subjected to the approximation of n-th power equation such as approximation of fifth power equation. A maximum potential difference ratio $V/V_0max$ obtained by subjecting the potential difference distribution to the approximation of fourth power equation is substituted for the master curve in order to find the dept $a^*$ of crack. Next, the aspect ratio $a^*/c^*$ of crack is found from the length $2c^*$ ($= 2c \times 20/t^*$) of crack in the surface corrected by the plate thickness, and is compared with the aspect ratio $a/c$ of the master curve. When they are not in agreement, a master curve is prepared again based on the relationship between the potential difference ratio $V/V_0$ and the aspect ratio $a/c$ to represent a relationship between the depth $a/t$ of crack and the potential difference ratio $V/V_0$ for the aspect ratio $a/c = a^*/c^*$. The maximum potential difference ratio $V/V_0max$ is substituted for the master curve to find the depth $a^*$ of crack. This operation is repeated until they are brought into agreement with each other, e.g., until the difference between $a/c$ and $a^*/c^*$ becomes smaller than 0.01. The potential difference ratio at each of the measuring positions is substituted for a master curve that represents the relationship between the depth $a/t$ of crack and the potential difference ratio $V/V_0$ for the aspect ratio of when it is brought into agreement, in order to determine the shape of the whole crack. In this case, the potential difference ratio at each of the measuring positions may be substituted or the distribution of potential difference ratios after subjected to approximation of n-th power equation may be substituted. Described below are the results that are concretely calculated relying upon the potential difference distribution around the crack shown in FIG. 32. The plate thickness is $t^* = 20.0$ mm and the distance between the measuring terminals is $d = 20$ mm. Here, the potential difference is found for each of the depths of cracks having various aspect ratios at a position $d^* = d \times 20/t^* = 20$ mm. The potential difference is measured in a manner that the crack is located at the center between the measuring electrodes. Therefore, the potential difference is found at a position $z = d^*/2 = 10$ mm, and relationships between the potential difference ratio $V/V_0$ and the aspect ratio $a/c$ are obtained as shown in FIG. 33. Using these relationships, master curves are prepared to represent relationships between the depth $a/t$ of crack and the potential difference ratio $V/V_0$ for the aspect ratio $a/c = 0.5$ as shown in FIG. 34. If the maximum potential difference ratio $V/V_0max = 1.30$ is substituted for the curve, there is obtained $a^*t = 0.76$ and whereby $a^* = 15.2$ mm. From $2c^* = 110$ mm, the aspect ratio of crack is $a^*/c^* = 15.2/55 = 0.276$.

Figure 35:
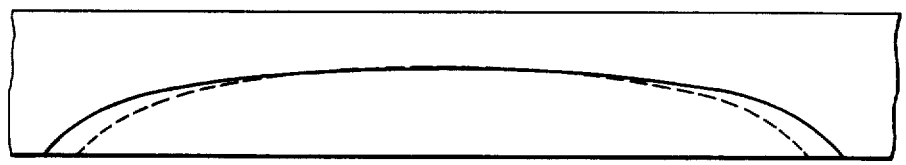
FIG. 35 is a diagram which compares the shape of crack used for the analysis with the shape of crack that is determined using the apparatus of FIGS. 23 and 24.

Next, a master curve is prepared for $a/c = 0.276$ to find the depth of crack: $a^* = 12.86$ mm and whereby $a^*/c^* = 0.234$. Again, a master curve is prepared for $a/c = 0.234$ to find the depth of crack. This time, $a^* = 1.24$ mm and $a^*/c^* = 0.225$. Furthermore, a master curve is prepared for $a/c = 0.225$ to find the depth of crack. In this case, there is obtained $a^* = 12.3$ mm and $a^*/c^* = 0.224$; i.e., the aspect ratio is nearly in agreement this time. FIG. 35 shows the corresponding between the shape of crack in the surface found ad described above and the shape of crack used in the analysis. Though the precision is not so high near the tips of crack in the surface, they are in very good agreement in other regions.

The above-mentioned method, however, can be adapted to the case where the crack is perpendicular to the electric field, but cannot be applied to the case where the crack is tilted as shown in FIG. 29. In such a case, coordinate points marked with squares and rhombuses in FIG. 29 are approximated to straight lines by the least square method to find an angle relative to the perpendicular direction and to find a length $2c^*$ of crack from the coordinates of two ends. Here, if an angle subtended by the direction normal to the crack and the direction of electric field is denoted by —, the potential difference ratio $V/V_0'$ become smaller than the potential difference ratio $V/V_0$ of when the crack is at right angles with the electric field, and the primary approximation becomes $V/V_0' = V/V_0 \cdot \cos —$. When the shape of crack is to be found by the above-mentioned method, therefore, the measured potential difference ratio $V/V_0'$ must be corrected by — and must be evaluated in terms of $V/V_0 = V/V_0'/\cos —$. Precision, however, decreases as the angle — exceeds 45°. Therefore, the shape is better detemined relying upon the measured results in the electric field where the angle — is smaller than 45°.

According to the apparatus for monitoring cracks of conduit of the fourth invention as described above, the position and shape of crack are detected by measuring the distribution of potential differences in one direction and in the other direction of a material to be inspected relying upon the measuring electrodes that are arranged in the form of a matrix on the peripheries of a portion of the material to be inspected maintaining an equal spacing in both directions. Therefore, integrity of the material can be precisely inspected.

What is claimed is:

1. A method of detecting the shape of a crack on a surface of material on which cracks may appear comprising:
providing a plurality of electrodes arranged in the form of a matrix on said surface, said electrodes being connected to serve both as power supplying electrodes and potential difference measuring electrodes;
switching a first pair of electrodes in said matrix to serve as power supplying electrodes while other electrodes in said matrix are switched for measuring the potential difference distribution;
thereafter switching a second pair of electrodes in said matrix to serve as power supplying electrodes while said first pair of electrodes are switched for measuring part of said potential difference distribution to thereby measure potential difference distribution in various directions and precisely determine a surface crack shape.

2. A method of detecting the shape of a crack on a surface of material on which cracks may appear comprising:
providing a plurality of electrodes arranged in the form of a matrix on said surface, said electrodes being connected to serve both as power supplying electrodes and potential difference measuring electrodes;
switching a first pair of electrodes in said matrix to serve as power supplying electrodes while other electrodes in said matrix are switched for measuring the potential difference distribution;
thereafter switching a second pair of electrodes in said matrix to serve as power supplying electrodes while said first pair of electrodes are switched for measuring part of said potential difference distribution; and
continuing said switching of yet different pairs of electrodes from said matrix to serve as power supplying electrodes while said first and second pairs of electrodes are switched for measuring part of said potential difference distribution to thereby measure potential difference distribution in various directions and precisely determine a surface crack shape.

3. In an apparatus for inspecting surface defects on a member comprising a current power supply;
a plurality of electrodes disposed on a defect containing surface of said member in the form of a matrix;
pairs of power supplying electrodes in said matrix for supplying a direct current from said current power supply onto the surface of said member containing said matrix;
pairs of potential difference-measuring electrodes in said matrix for measuring potential differences inside one of pairs of feeder terminals and said pairs of power supplying electrode;
a defect determining unit for determining surface defects relaying upon the measured potential difference signals;
means wherein said power supplying electrodes are sequentially selected from a plurality of different pairs of electrodes in said matrix to enable the direction of current to be freely changed relative to the defect and the power supplying pairs of electrodes in said matrix used as potential difference measuring electrodes when not connected to said power supply.

4. An apparatus for inspecting surface defects according to claim 3, wherein at least the power supplying electrodes are arranged in the form of a matrix.

5. In a method of inspecting the shape of a defect on a surface by:
providing a plurality of electrodes arranged in the form of a matrix on said surface, said electrodes being connectable to serve both as power supplying electrodes and potential difference measuring electrodes;
applying electric power to the surface of a structure to be inspected through a first pair of power supplying electrodes in said matrix that are spaced apart from each other;
measuring a potential difference by one or more pairs of potential difference-measuring electrodes in said matrix between said pair of power supplying electrodes;
subsequently applying electric power to a second pair of electrodes from said matrix while using said first pair of electrodes as potential difference-measuring electrodes in the matrix on the surface of said structure in which defects may have occurred; and
switching matrix electrodes to be served with electric power and electrodes for measuring the potential difference to measure the distribution of potential differences in order to detect the position where a defect has occurred and the shape of said defect.

6. A method of inspecting a surface for defects according to claim 5, wherein electrodes that serve as both power supplying electrodes and measuring electrodes are arranged on a surface of a conduit in the form of a matrix so that the electrodes are in parallel line both in the axial direction and in the circumferential direction of said conduit, said method further comprising the steps of:
applying a direct current to electrodes arranged at both ends in the axial direction of said conduit so that current flow is across a line of electrodes extending in a circumferential direction; and
measuring a distribution of potential differences among the electrodes that are neighboring to each other in the axial direction between the electrodes arranged in between, in order to detect the position and shape of a crack in the circumferential direction.

7. A method of inspecting a surface for defects according to claim 5, wherein electrodes that serve as both power supplying electrodes and measuring electrodes are arranged on a surface of a conduit in the form of a matrix so that the electrodes are in parallel lines both in the axial direction and in the circumferential direction, said method further comprising:

applying a direct current to a line of electrodes arranged in the axial direction and to another line of electrodes opposed to the electrode lines being separated away thereform by 180 degrees around the conduit perimeter; and measuring a distribution of potential differences among electrodes that are neighboring to each other in the circumferential direction between the electrodes, in order to detect the position and shape of a crack in the axial direction.

8. A method of inspecting a surface for defects according to claim 5, wherein electrodes that serve as both power supplying electrodes and measuring electrodes are arranged on a surface of a conduit in the form of a matrix so that the electrodes are in parallel lines both in the axial direction and in the circumferential direction, said method further comprising:

applying a direct current across a line of electrodes arranged in the axial direction and another line of electrodes opposed to said electrode line, said electrode lines being separated therefrom by 180 degrees;

measuring a distribution of potential differences among electrodes that are neighboring in the circumferential direction except the potential difference between the electrodes through which the direct current is supplied and except the potential differences between the neighboring electrodes;

applying a direct current across two sets of lines of electrodes that are respectively separated away by 90 degrees from the line of electrodes through which said direct current is supplied; and measuring a distribution of potential differences among electrodes neighboring to each other in the circumferential direction except the potential difference between the electrodes through which the direct current is supplied and except the potential differences between the neighboring electrodes, whereby a distribution of potential differences is measured in the circumferential direction under a uniform electric field condition to detect the position and shape of a crack disposed generally along the axial direction.

9. A method inspecting a surface for defects according to claim 5, wherein electrodes that serve as both power supply electrodes and measuring electrodes are arranged on the outer surface of a conduit in the form of a matrix so that the electrodes are in parallel lines both in the axial direction and in the circumferential direction, said method further comprising:

applying a direct current from lines of electrodes at both ends in the axial direction to measure potential differences among the electrodes that are neighboring to each other in the axial direction; and applying a direct current across the lines of electrodes in the circumferential direction to measure potential differences among the electrodes that are neighboring to each other in the circumferential direction, in order to detect the shape of a crack that is tilted relative to the axial direction or the circumferential direction based upon the distribution of potential differences in the axial direction and in the circumferential direction.

* * * * *